(12) United States Patent
Nickisch et al.

(10) Patent No.: US 9,850,273 B2
(45) Date of Patent: Dec. 26, 2017

(54) COMBINATION OF ESTROGENS PLUS ANTIPROGESTINS WITH SIGNIFICANT PARTIAL AGONISTIC EFFECT AS AN EFFECTIVE TREATMENT OF MENOPAUSAL SYMPTOMS AND FOR PREVENTION OF THE OCCURRENCE OF BREAST CANCER

(71) Applicant: Evestra, Inc., San Antonio, TX (US)

(72) Inventors: Klaus Nickisch, Berlin (DE); Bindu Santhamma, San Antonio, TX (US); Hareesh Nair, San Antonio, TX (US); Walter Elger, Berlin (DE)

(73) Assignee: Evestra, Inc., San Antonio, TX (US)

( * ) Notice: Subject to any disclaimer, the term of this patent is extended or adjusted under 35 U.S.C. 154(b) by 0 days.

(21) Appl. No.: 14/958,230

(22) Filed: Dec. 3, 2015

(65) Prior Publication Data
US 2016/0159852 A1  Jun. 9, 2016

Related U.S. Application Data

(60) Provisional application No. 62/087,061, filed on Dec. 3, 2014.

(51) Int. Cl.
| | | |
|---|---|---|
| C07J 71/00 | (2006.01) | |
| C07J 17/00 | (2006.01) | |
| C07J 21/00 | (2006.01) | |
| C07J 41/00 | (2006.01) | |
| C07J 7/00 | (2006.01) | |
| A61K 31/566 | (2006.01) | |
| A61K 31/58 | (2006.01) | |
| C07J 43/00 | (2006.01) | |

(52) U.S. Cl.
CPC ......... *C07J 71/0005* (2013.01); *A61K 31/566* (2013.01); *A61K 31/58* (2013.01); *C07J 17/00* (2013.01); *C07J 21/00* (2013.01); *C07J 43/003* (2013.01); *C07J 7/003* (2013.01); *C07J 21/006* (2013.01); *C07J 41/005* (2013.01); *C07J 71/001* (2013.01)

(58) Field of Classification Search
CPC ...... C07J 71/001; C07J 71/0005; C07J 17/00; C07J 21/00; C07J 7/003; C07J 21/006; C07J 41/005

See application file for complete search history.

(56) References Cited

U.S. PATENT DOCUMENTS

| | | | | |
|---|---|---|---|---|
| 5,468,736 A | * | 11/1995 | Hodgen | A61K 31/565 514/170 |
| 6,479,535 B1 | | 11/2002 | Pickar et al. | |
| 6,740,645 B1 | * | 5/2004 | Cook | C07J 41/0083 514/176 |
| 2010/0273759 A1 | * | 10/2010 | Nickisch | C07J 21/00 514/173 |

FOREIGN PATENT DOCUMENTS

| | | |
|---|---|---|
| WO | 98/05679 | 2/1998 |
| WO | 99/45022 | 9/1999 |
| WO | 2005/092912 | 10/2005 |

OTHER PUBLICATIONS

International Search Report/Written Opinion for PCT Application No. PCT/US2015/063734 dated May 10, 2016.
Wagner et al. "16a-substituted analogs of the antiprogestin RU486 induce a unique conformation in the human progesterone receptor resulting in mixed agonist activity" Proc. Natl. Acad. Sci. USA (1996) vol. 93, pp. 8739-8744.
Rewinkel et al. "11-(Pyridinylphenyl)steroids—A new class of mixed-profile progesterone agonists/antagonists" Bioorganic & Medicinal Chemistry (2008) vol. 16, pp. 2753-2763.

* cited by examiner

*Primary Examiner* — Sahar Javanmard
(74) *Attorney, Agent, or Firm* — Meyertons, Hood, Kivlin, Kowert & Goetzel, P.C.; Mark R. DeLuca

(57) ABSTRACT

Described herein are compositions and methods for hormone replacement therapy that address the shortcomings of the existing methods. Described herein are pharmaceutically effective partial agonistic antiprogestins. The combined application of estrogens (such as estradiol, estriol and conjugated estrogens) and the disclosed partial agonistic antiprogestins can be used in hormone replacement therapy.

13 Claims, 10 Drawing Sheets

COMBINATION OF ESTROGENS PLUS ANTIPROGESTINS WITH SIGNIFICANT PARTIAL AGONISTIC EFFECT AS AN EFFECTIVE TREATMENT OF MENOPAUSAL SYMPTOMS AND FOR PREVENTION OF THE OCCURRENCE OF BREAST CANCER

PRIORITY CLAIM

This application claims priority to U.S. Provisional Application Ser. No. 62/087,061 entitled "Combination of estrogens plus antiprogestins with significant partial agonistic effect as an effective treatment of menopausal symptoms and for prevention of the occurrence of breast cancer" filed Dec. 3, 2014, which is incorporated herein by reference in its entirety.

BACKGROUND OF THE INVENTION

1. Field of the Invention

The invention generally relates to the use of estrogens and antiprogestins for the treatment of hormone related conditions.

2. Description of the Relevant Art

With the onset of menopause in women, so-called menopausal symptoms occur owing to altered hormone production, reduced estrogen production lead to increased risk of osteoporosis and other symptoms like hot flashes, sweating and mood swings.

Hormone replacement therapy (HRT) with estrogens or an estrogen/progestin combination is currently the standard method of treatment for such symptoms. Benefits and risks of menopausal estrogen and/or progestin use have been well documented.

One of the risks of HRT is an increased risk of endometrial carcinomas. The use of simultaneous treatment of estrogen with a progestin can mitigate these risks. Progestins suppress the stimulating effect on the endometrium caused by estrogens.

One point of great concern of such combination therapy (estrogen/progestin treatments) is that many progestins lead to an increase in breast cancer risk. Thus, the current therapies for reducing or preventing symptoms of menopause are not ideal.

The search for alternative therapies lead to a combination of an antioestrogen with an antiprogestin and the use of a combination of estrogens and antiprogestins in a sequential manner.

For numerous antiprogestins, antiproliferative activity in vitro and antitumor effect in animal models has been reported for compounds such as RU 486, Onapristone, and ZK 230 211. All the reported compounds however belong to the class of pure progesterone receptor antagonists that lack partial agonistic activity. Such compounds are therefore not suitable for a combination therapy with estrogens. Such compounds lead to side effects of unopposed estrogenicity, such as endometrial hyperplasias or endometrial cancer.

Compounds possessing both agonistic and antagonistic activity have been reported in the past. However, the use of such compounds in a combination therapy with estrogens has not, to our knowledge, been described.

Another approach to an improved treatment of menopausal symptoms is described in U.S. Pat. No. 6,479,535. A combination of conjugated estrogens with estrogen antagonists (e.g., Bazedoxifene) was described. This combination has been described to have, besides positive effects on menopausal symptoms, the ability to block the growth of occult breast cancer neoplasms in postmenopausal women, and thus should lead to an overall reduction in tumor incidence. The disadvantage of conjugated estrogens with estrogen antagonists is inferior bleeding profile compared to standard estradiol progestin combinations. In a group of postmenopausal women the incidence of irregular bleeding during cycle 9 is 11% for a 1 mg E2/0.5 mg META combination and 25.8% for 0.625 mg CEE (conjugated estrogen)/5 mg MPA. The cumulative rate of amenorrhea in postmenopausal women is around 90% and around 80% in perimenopausal women. Bazedoxifene/conjugated estrogens showed only an 83% incidence of amenorrhea in the first year of treatment in postmenopausal women.

In summary it can be concluded that there is still a high medical need for an effective treatment of menopausal complaints with an excellent bleeding control for postmenopausal and perimenopausal women. In addition such treatment should have a preventive effect on the occurrence of breast cancer.

SUMMARY OF THE INVENTION

Described herein are compositions and methods for hormone replacement therapy that address the shortcomings of the existing methods. Described here are pharmaceutically effective compounds that exhibit simultaneously strong agonistic and antagonistic effects on the progesterone receptor. The disclosed compounds exhibit EC 50 values in the nano- to subnano-molecular range in the transactivation assay with R5020 and RU-486 as control compounds.

In another embodiment, the combined application of estrogens (such as estradiol, estriol and conjugated estrogens) and the disclosed antiprogestins can be used in hormone replacement therapy.

In another embodiment, the combined application of estrogens (such as estradiol, estriol and conjugated estrogens) and the disclosed antiprogestins shows an antiproliferatory effect on breast cancer cells and therefore has the ability to reduce occurrence of breast cancer in women taking such product.

The pharmaceutical agents disclosed herein, therefore, are suitable both for preventive and curative use in hormone replacement therapy.

BRIEF DESCRIPTION OF THE DRAWINGS

Advantages of the present invention will become apparent to those skilled in the art with the benefit of the following detailed description of embodiments and upon reference to the accompanying drawings in which.

Figure 1A:
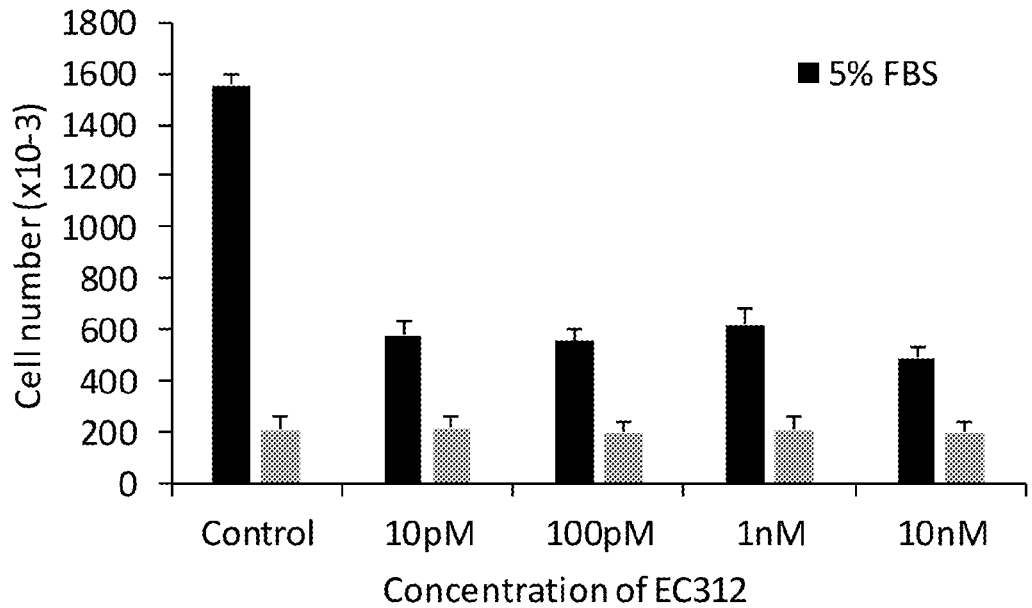
FIGS. 1A-1B depict the antiestrogenic effect of EC312 and EC313 on cell growth in the presence and absence of endogenous estrogens.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

In an embodiment, a pharmaceutical composition comprises an estrogen and a partial agonistic antiprogestin. The combined application of estrogens (such as estradiol, estriol and conjugated estrogens) and partial agonistic antiprogestin can be used in hormone replacement therapy. Additionally, the combined application of estrogens and the disclosed antiprogestins shows an antiproliferatory effect on breast cancer cells and therefore has the ability to reduce occurrence of breast cancer in women taking such product. The pharmaceutical compositions disclosed herein, therefore, are suitable both for preventive and curative use in hormone replacement therapy.

As used herein, a partial agonistic antiprogestin is a compound that exhibits selective stimulation (agonistic) progesterone activity and inhibitory (antagonistic) progesterone activity in different tissues. For example, in some embodiments, a partial agonistic antiprogestin has: an EC 50 of less than 25 nM in a progesterone transactivation assay, carried out on human breast cancer (T47D) cells, for agonistic activity; and an EC 50 of less than 10 nM in a progesterone transactivation assay, carried out on human breast cancer (T47D) cells, for antagonistic activity. In an embodiment, the partial agonistic antiprogestin has an EC 50 between 1 nM to 10 nM in a progesterone transactivation assay, carried out on human breast cancer (T47D) cells, for agonistic activity. In an embodiment, the partial agonistic antiprogestin has an EC 50 of between 0.1 nM and 5 nM in a progesterone transactivation assay, carried out on human breast cancer (T47D) cells, for antagonistic activity. In an embodiment, the partial agonistic antiprogestin has an EC 50 between 1 nM to 10 nM in a progesterone transactivation assay, carried out on human breast cancer (T47D) cells, for agonistic activity; and wherein the partial agonistic antiprogestin has an EC 50 of between 0.1 nM and 5 nM in a progesterone transactivation assay, carried out on human breast cancer (T47D) cells, for antagonistic activity. The partial agonistic antiprogestin, in some embodiments, shows a ratio of the EC 50 values between agonistic and antagonistic activity in a progesterone transactivation assay, carried out on human breast cancer (T47D) cells, of between 1:0.5 to 1:10.

Other tests can be used to identify partial agonistic antiprogestins. For example a partial agonistic antiprogestin is classified as a pure mesoprogestin in the Guinea pig model. Furthermore, a partial agonistic antiprogestin shows a McPhail index of >2 at doses >1 mg/day.

As used herein, an "estrogen" refers to any of various natural or synthetic compounds that stimulate the development of female secondary sex characteristics and promote the growth and maintenance of the female reproductive system, or any other compound that mimics the physiological effect of natural estrogens. Estrogens also include compounds that can be converted to active estrogenic compounds in the uterine environment. Estrogens include, but are not limited to, estradiol (17β-estradiol), estridiol acetate, estradiol benzoate, estridiol cypionate, estridiol decanoate, estradiol diacetate, estradiol heptanoate, estradiol valerate, 17α-estradiol, estriol, estriol succinate, estrone, estrone acetate, estrone sulfate, estropipate (piperazine estrone sulfate, mestranol, quinestrol, and nitrated estrogen derivatives. Nitrated estrogen derivatives are described in U.S. Pat. No. 5,554,603 to Kim et al. which is incorporated herein by reference.

Compounds possessing both agonistic and antagonistic activity include compounds having the formula (I)

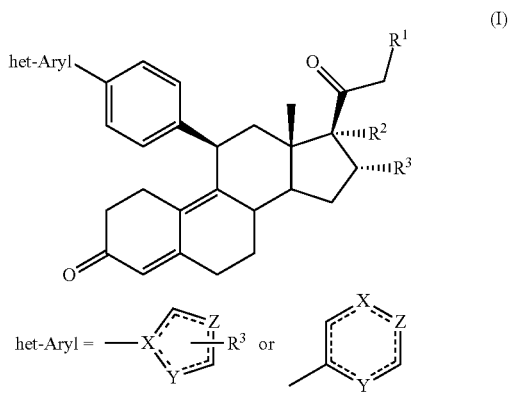

X = N, C
Y = C, N, O, S
Z = C, N, O, S
$R^1$ = H, alkyl, hydroxy alkyl
$R^2$ = H, alkyl, hydroxyl, hydroxy acetyl, hydroxy alkyl
$R^3$ = H, alkyl, cycloalkyl, alkenyl, alkynyl, halides, alkenyl halides wherein at least one of X, Y, and Z is not a carbon atom.

In some embodiments, compounds possessing both agonistic and antagonistic activity include compounds having the formula (I), in which:

Het-Aryl is:

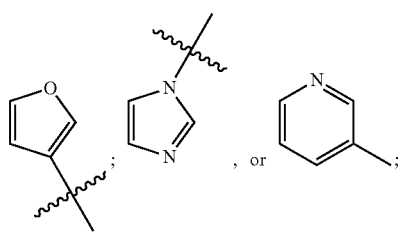

and $R^1$ is H; $R^2$ is H; and $R^3$ is $CH_3$; $C_2H_5$; and $C_2H_3$

Specific examples of structural formula (I) include the following compounds:

EC343

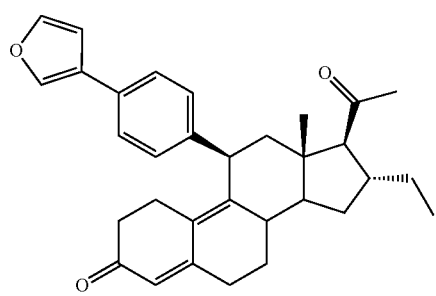

EC345

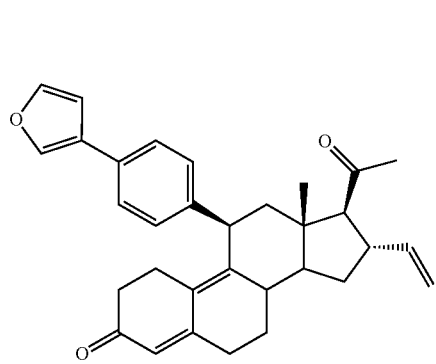

EC346

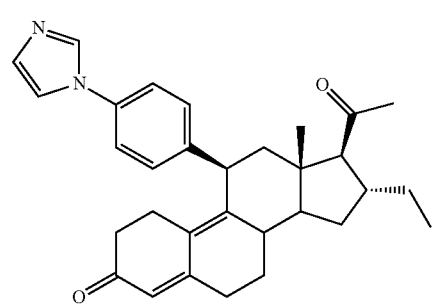

EC347

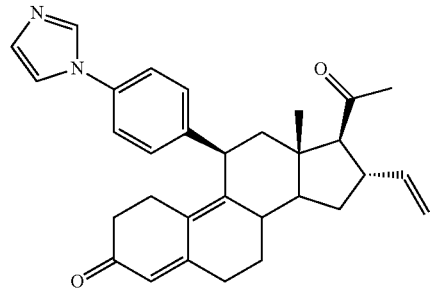

EC342

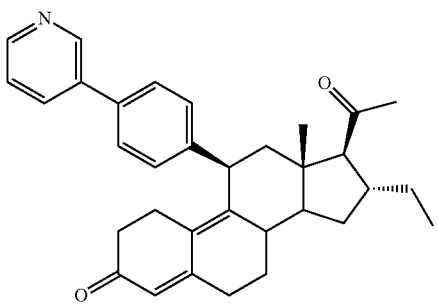

EC344

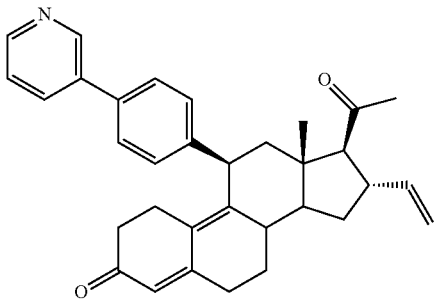

EC348

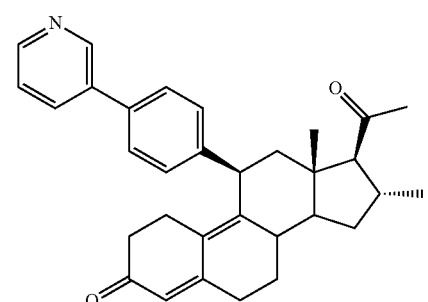

Other partial agonistic antiprogestins include compounds EC 312, EC 313, EC 317, EC 336, or mixtures thereof.

EC-312

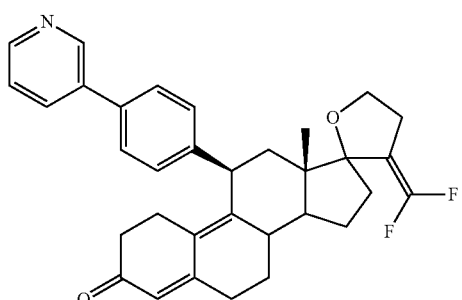

EC-313

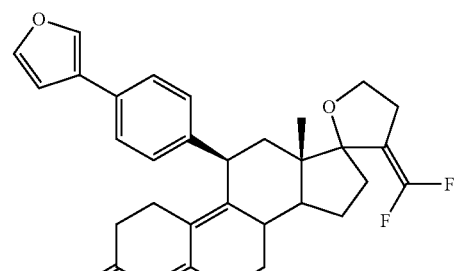

EC-336

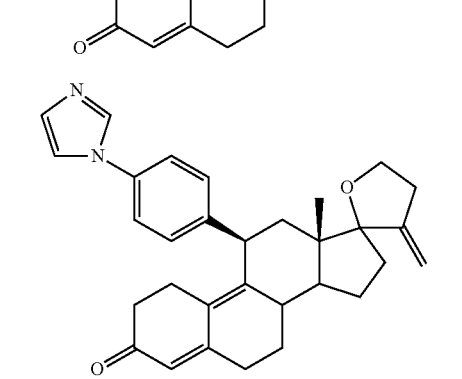

EC-317

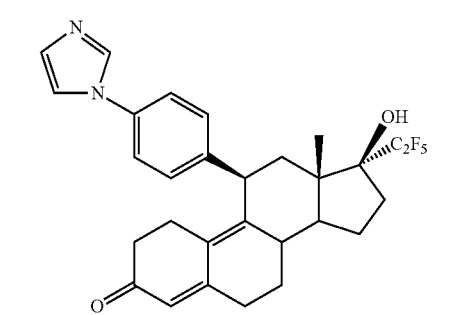

The pharmaceutical composition may be in any suitable form for administration to the subject. While oral dosage forms may be a preferred embodiment of delivery, it should be understood that any suitable route of administration may be employed for providing a patient with an effective dosage of the composition described herein. For example, rectal, topical, parenteral, ocular, pulmonary, nasal, and the like may be employed. Dosage forms include tablets, troches, dispersions, suspensions, solutions, capsules, creams, ointments, aerosols, and the like. The pharmaceutical composition may include any combination of excipients, fillers, binders, etc. necessary to provide the composition in a form suitable for administration.

In an embodiment, a method of monotherapy for the treatment of endometriosis and fibroids in a subject comprises administering to a subject who would benefit from such treatment a therapeutically effective amount of a pharmaceutical composition comprising a partial agonistic antiprogestin having the general structure of:

[Structure diagram]

het-Aryl = [structure] or [structure]

X = N, C
Y = C, N, O, S
Z = C, N, O, S
$R^1$ = H, alkyl, hydroxy alkyl
$R^2$ = H, alkyl, hydroxyl, hydroxy acetyl, hydroxy alkyl
$R^3$ = H, alkyl, cycloalkyl, alkenyl, alkynyl, halides, alkenyl halides wherein at least one of X, Y, and Z is not a carbon atom.

In an embodiment, the partial agonistic antiprogestin is EC343, EC 344, EC 345, EC 346, or mixtures thereof.

In an embodiment, a method of monotherapy for the treatment of endometriosis and fibroids in a subject comprises administering to a subject who would benefit from such treatment a therapeutically effective amount of a pharmaceutical composition comprising a partial agonistic antiprogestin, wherein the partial agonistic antiprogestin is EC 312, EC 313, EC 317, EC 336, or mixtures thereof.

EC-312

[Structure diagram]

EC-313

[Structure diagram]

-continued

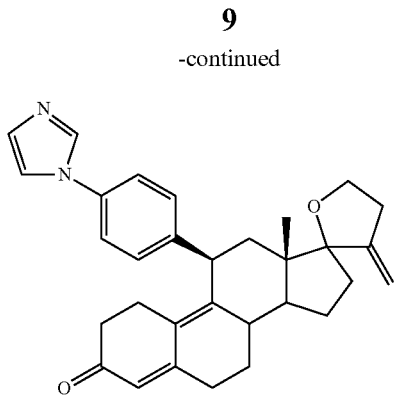

EC-336

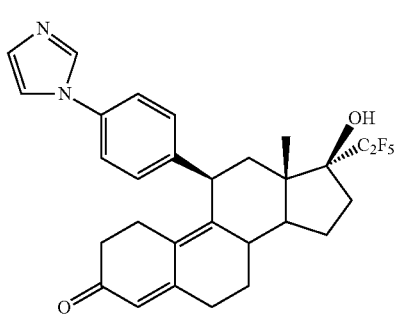

EC-317

Synthesis of these compounds may be accomplished according to the following schemes.

EC343 was synthesized by following the scheme outlined below.

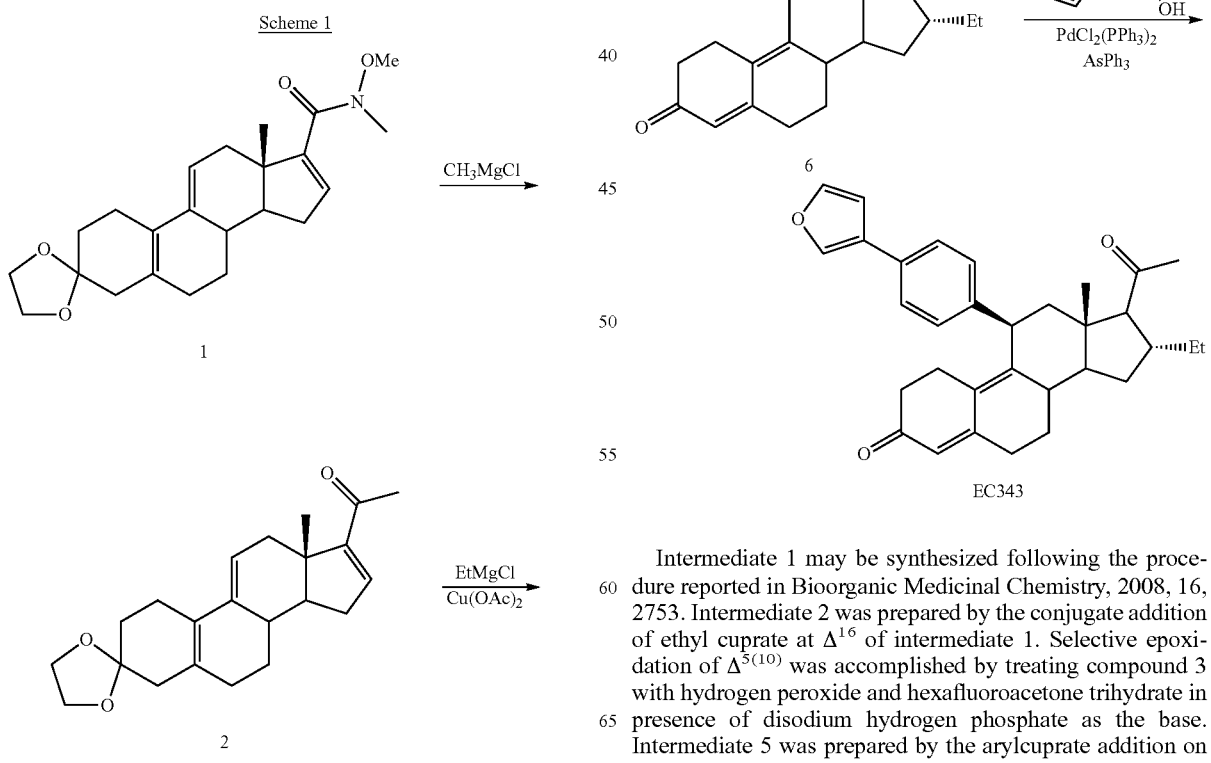

Intermediate 1 may be synthesized following the procedure reported in Bioorganic Medicinal Chemistry, 2008, 16, 2753. Intermediate 2 was prepared by the conjugate addition of ethyl cuprate at $\Delta^{16}$ of intermediate 1. Selective epoxidation of $\Delta^{5(10)}$ was accomplished by treating compound 3 with hydrogen peroxide and hexafluoroacetone trihydrate in presence of disodium hydrogen phosphate as the base. Intermediate 5 was prepared by the arylcuprate addition on 4 generated by the reaction of 1,4-diiodo benzene, isopropyl magnesium chloride and catalytic amounts of cuprous chloride. The aryl iodo derivative 5 obtained was hydrolyzed in presence of acid to give intermediate 6 which was subjected to a Suzuki coupling with furan 3-boronic acid in presence of palladium catalyst to furnish EC343.

Synthesis of EC345 was accomplished by following the steps outlined in Scheme 2

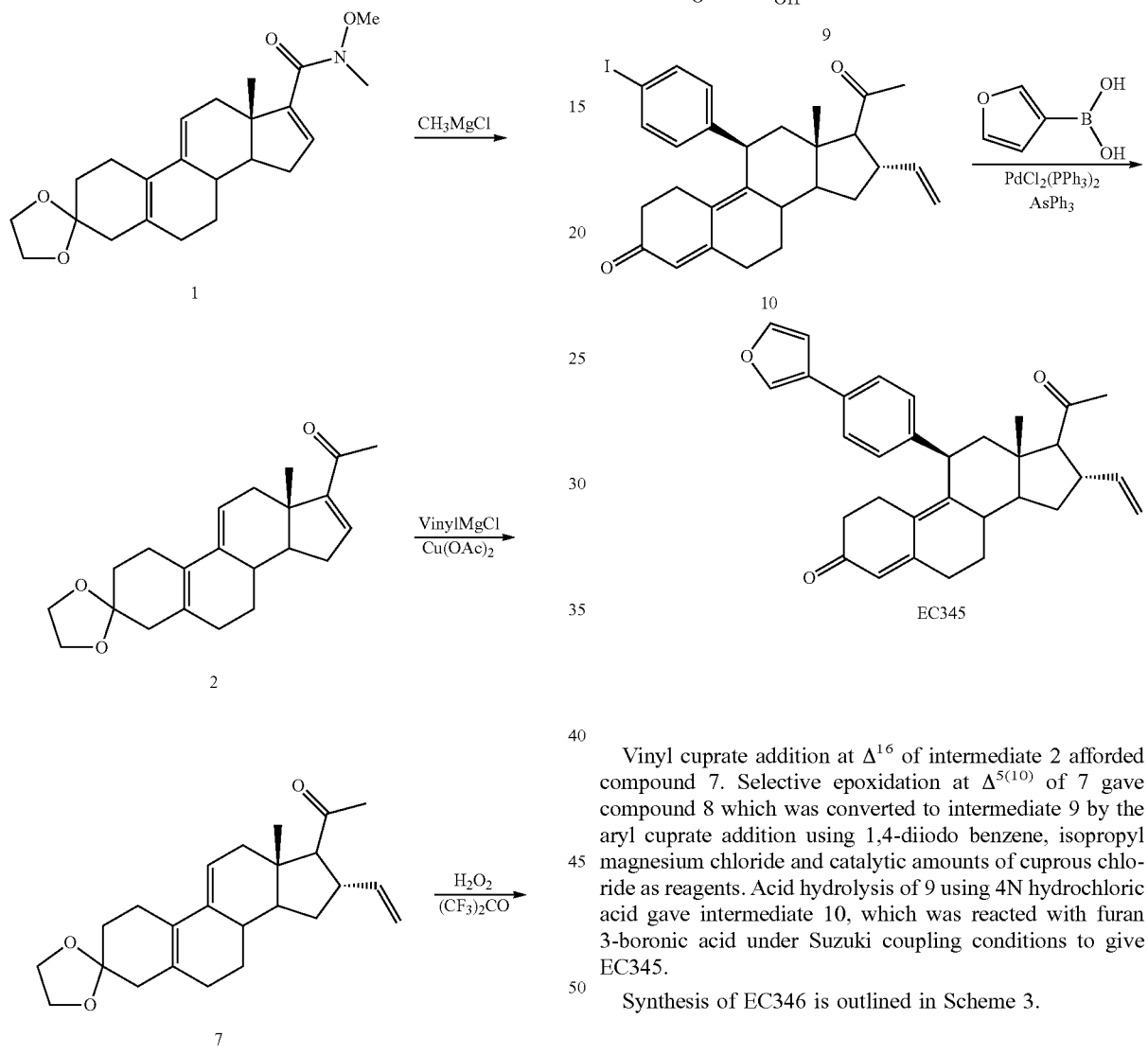

Vinyl cuprate addition at $\Delta^{16}$ of intermediate 2 afforded compound 7. Selective epoxidation at $\Delta^{5(10)}$ of 7 gave compound 8 which was converted to intermediate 9 by the aryl cuprate addition using 1,4-diiodo benzene, isopropyl magnesium chloride and catalytic amounts of cuprous chloride as reagents. Acid hydrolysis of 9 using 4N hydrochloric acid gave intermediate 10, which was reacted with furan 3-boronic acid under Suzuki coupling conditions to give EC345.

Synthesis of EC346 is outlined in Scheme 3.

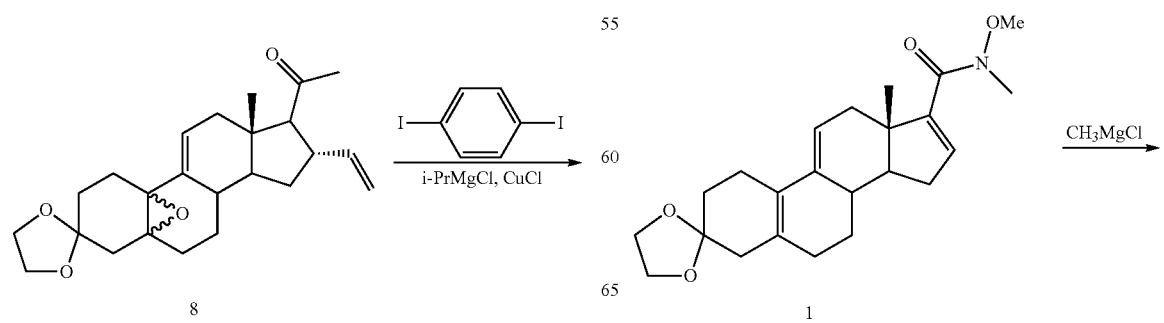

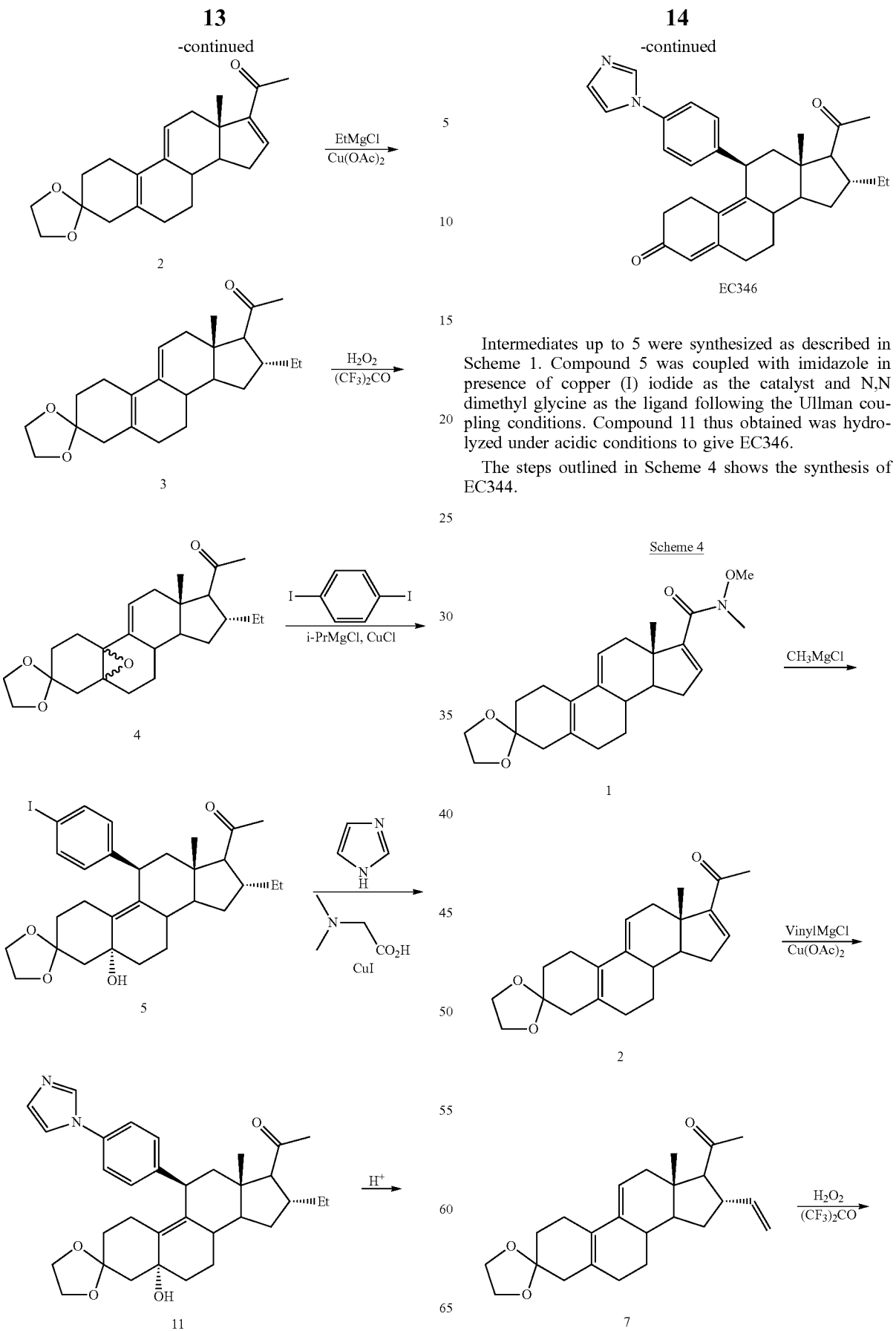
Intermediates up to 5 were synthesized as described in Scheme 1. Compound 5 was coupled with imidazole in presence of copper (I) iodide as the catalyst and N,N dimethyl glycine as the ligand following the Ullman coupling conditions. Compound 11 thus obtained was hydrolyzed under acidic conditions to give EC346.
The steps outlined in Scheme 4 shows the synthesis of EC344.

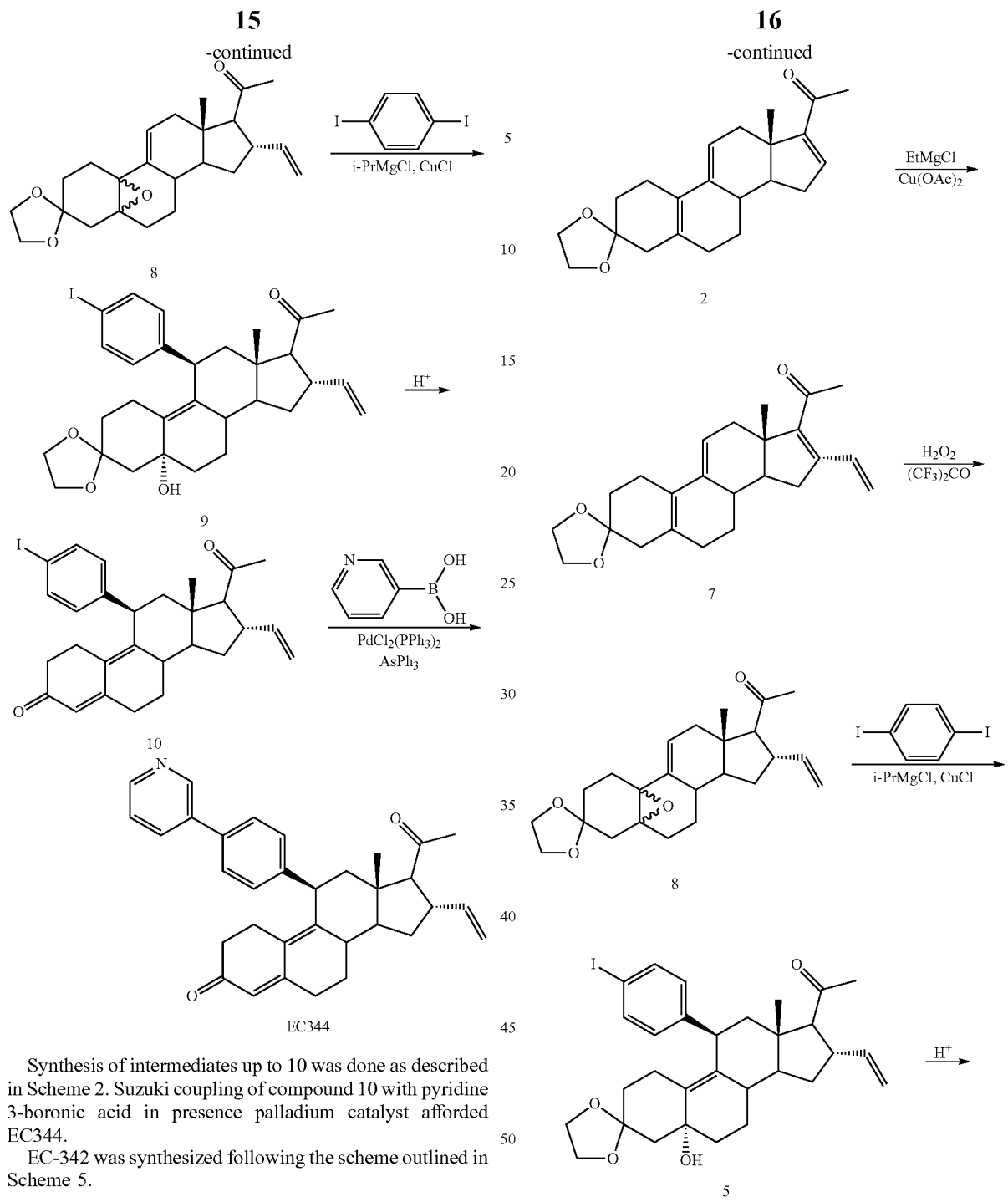
Synthesis of intermediates up to 10 was done as described in Scheme 2. Suzuki coupling of compound 10 with pyridine 3-boronic acid in presence palladium catalyst afforded EC344.
EC-342 was synthesized following the scheme outlined in Scheme 5.
Scheme 5
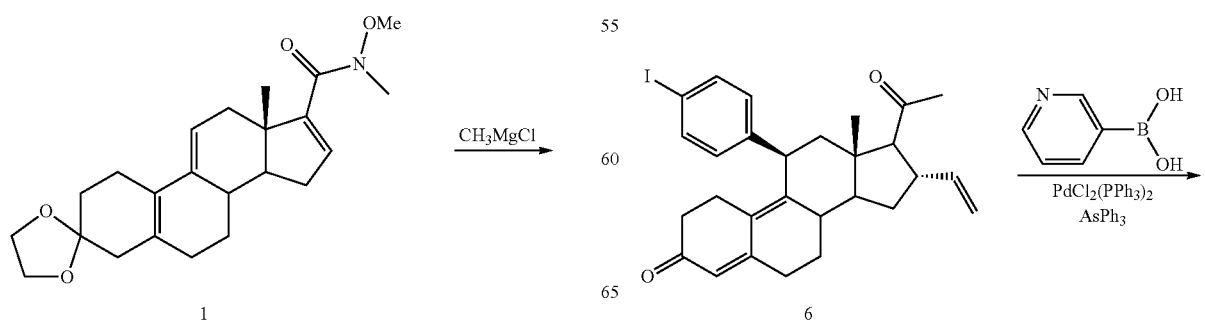

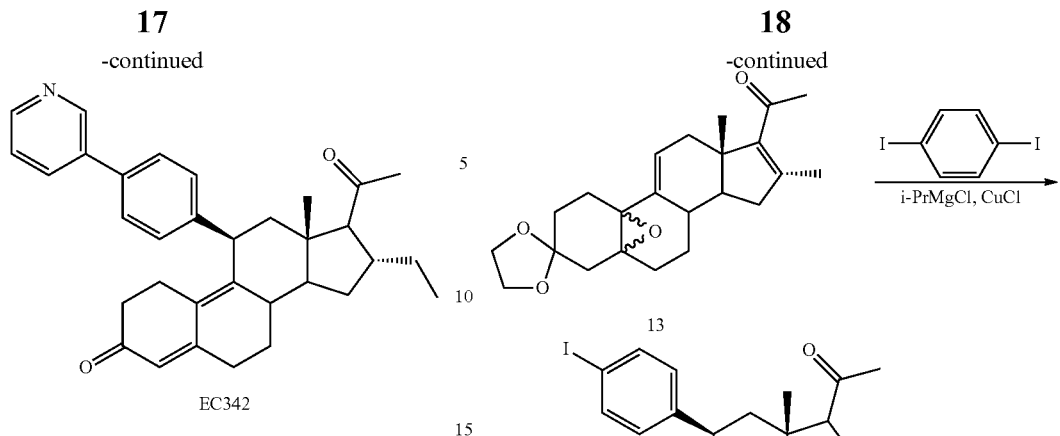

Synthesis of compounds up to 6 was accomplished as discussed under Scheme 1. Suzuki coupling of 6 with pyridine 3-boronic acid in presence of palladium catalyst afforded EC-342. Synthesis of EC-348 was done following the steps outlined in Scheme 6.

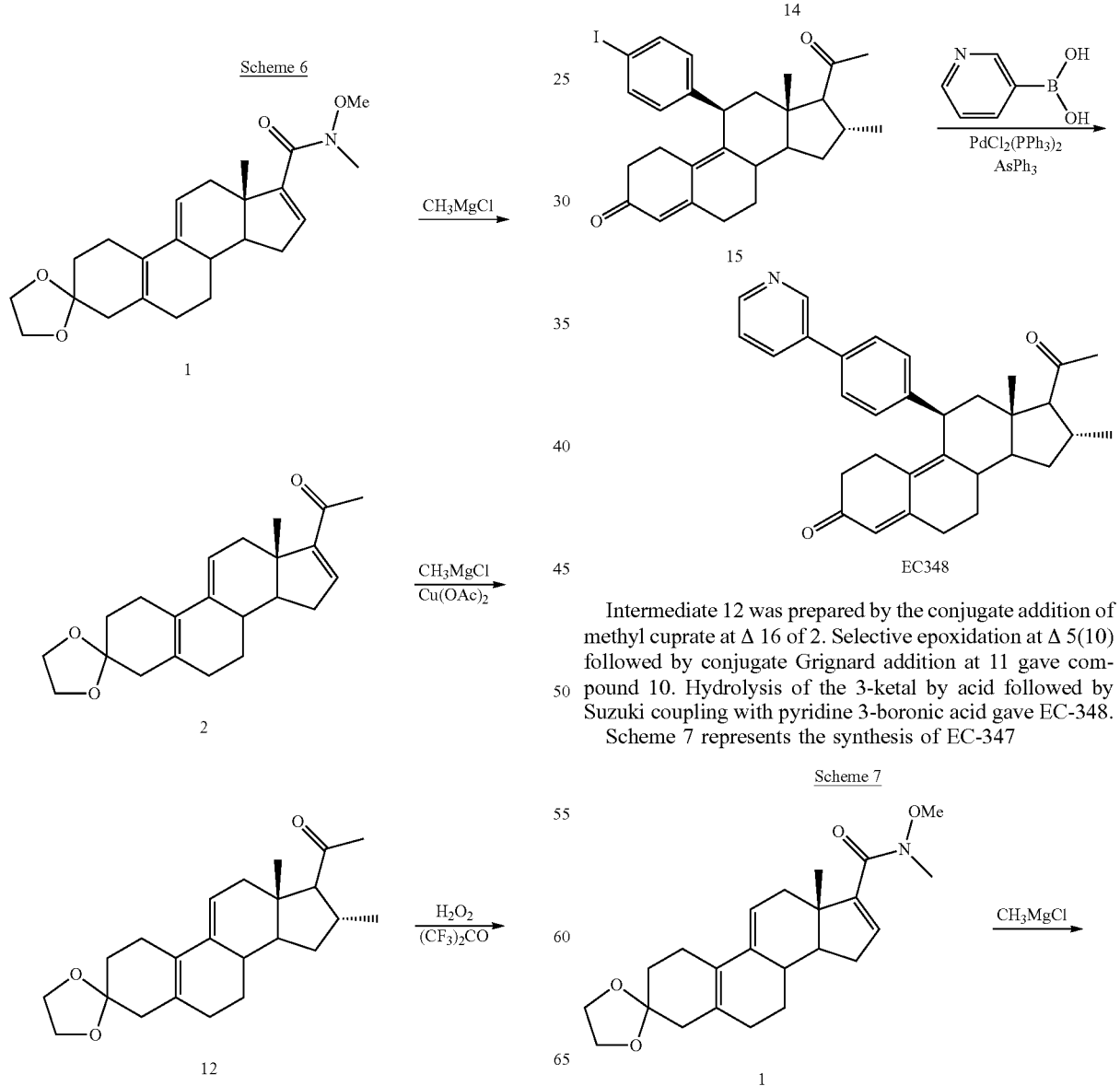

Intermediate 12 was prepared by the conjugate addition of methyl cuprate at Δ 16 of 2. Selective epoxidation at Δ 5(10) followed by conjugate Grignard addition at 11 gave compound 10. Hydrolysis of the 3-ketal by acid followed by Suzuki coupling with pyridine 3-boronic acid gave EC-348.

Scheme 7 represents the synthesis of EC-347

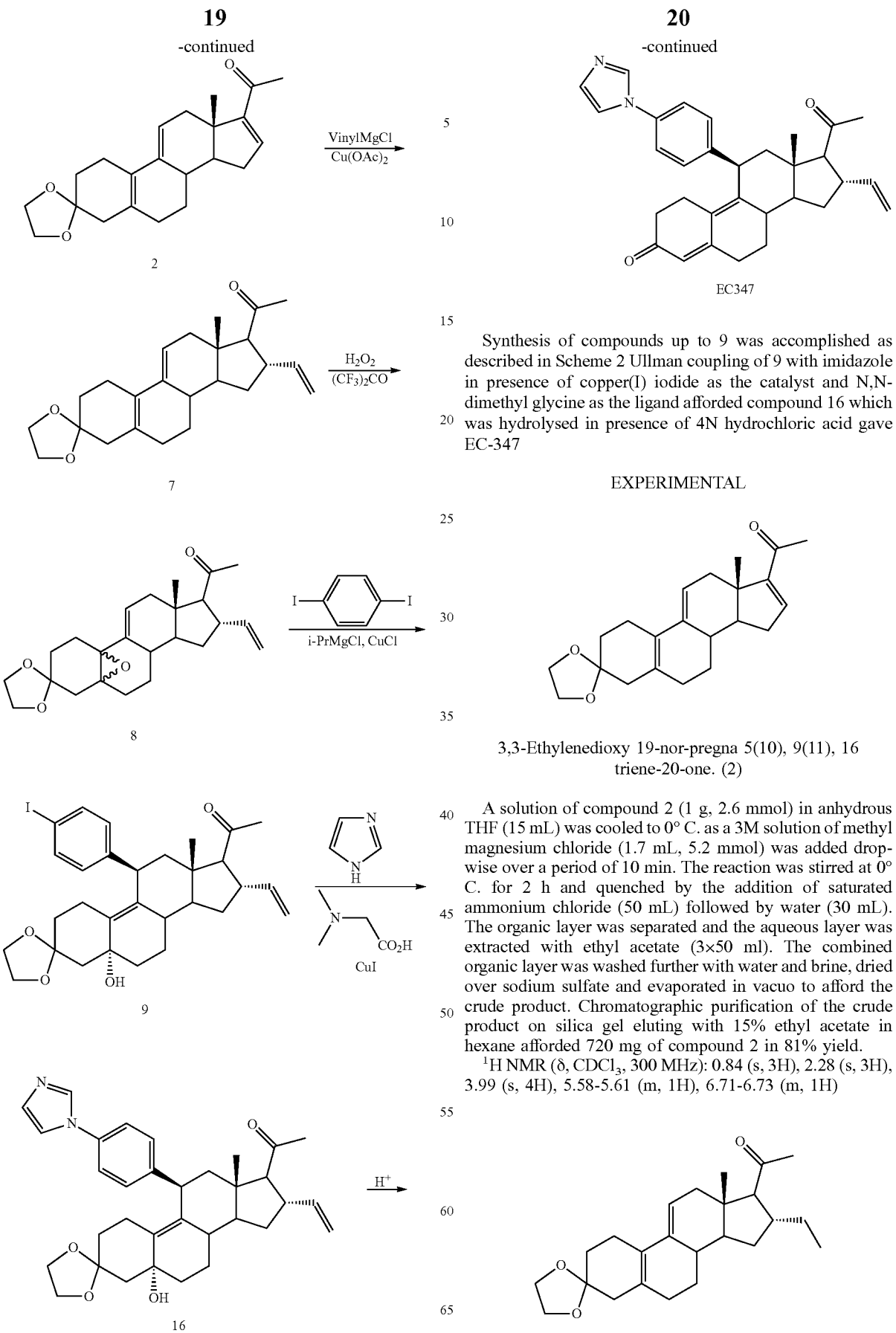

Synthesis of compounds up to 9 was accomplished as described in Scheme 2 Ullman coupling of 9 with imidazole in presence of copper(I) iodide as the catalyst and N,N-dimethyl glycine as the ligand afforded compound 16 which was hydrolysed in presence of 4N hydrochloric acid gave EC-347

EXPERIMENTAL 3,3-Ethylenedioxy 19-nor-pregna 5(10), 9(11), 16 triene-20-one. (2)

A solution of compound 2 (1 g, 2.6 mmol) in anhydrous THF (15 mL) was cooled to 0° C. as a 3M solution of methyl magnesium chloride (1.7 mL, 5.2 mmol) was added dropwise over a period of 10 min. The reaction was stirred at 0° C. for 2 h and quenched by the addition of saturated ammonium chloride (50 mL) followed by water (30 mL). The organic layer was separated and the aqueous layer was extracted with ethyl acetate (3×50 ml). The combined organic layer was washed further with water and brine, dried over sodium sulfate and evaporated in vacuo to afford the crude product. Chromatographic purification of the crude product on silica gel eluting with 15% ethyl acetate in hexane afforded 720 mg of compound 2 in 81% yield.

$^1$H NMR (δ, CDCl$_3$, 300 MHz): 0.84 (s, 3H), 2.28 (s, 3H), 3.99 (s, 4H), 5.58-5.61 (m, 1H), 6.71-6.73 (m, 1H)

3,3-Ethylenedioxy-16α-ethyl-19-nor-pregna 5(10), 9(11)diene-20-one. (3)

A solution of Copper (II) acetate (263 mg, 1.45 mmol) in anhydrous THF (170 mL) was cooled to 0° C. as a 2M solution of ethyl magnesium bromide in THF (22 mL, 43.4 mmol) was added dropwise. A solution of compound 2 (4.93 g, 14.47 mmol) together with chlorotrimethyl silane (7.86 g, 72.35 mmol) in THF (50 mL) was added dropwise keeping the temperature below 1° C. After an hour at 0° C., 7.2 mL of ethyl magnesium bromide was added and the reaction was stirred for 30 min. The reaction was quenched by the addition of saturated ammonium chloride solution (50 mL). Extracted with ethyl acetate (3×50 mL) and the combined organic layer were washed once with water, brine and dried over sodium sulfate. The solvent was removed under vacuum to obtain the crude product, which on purification by chromatography on SiO$_2$ column eluting with 15% ethyl acetate in hexane gave 5.21 g (97%) of required product 3 as a pale yellow solid.

$^1$H NMR (δ, CDCl$_3$, 300 MHz): 0.62 (s, 3H), 0.83 (t, J=6 Hz, 3H), 2.28 (s, 3H), 3.98 (s, 4H), 5.55-5.61 (m, 1H).

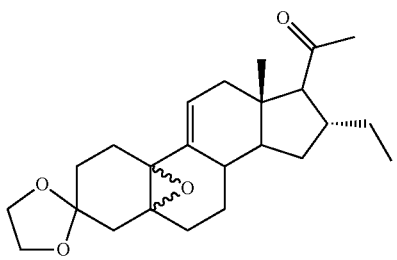

3,3-Ethylenedioxy-16α-ethyl-5,10-epoxy-19-nor-pregn-9(11)-ene-20-one. (4)

To a solution of compound 3 (5 g, 13.5 mmol) in dichloromethane (50 ml) was added hexafluoroacetone trihydrate (3.6 g, 16.2 mmol) and Na$_2$HPO$_4$ (3.8 g, 27 mmol). This suspension was vigorously stirred and cooled to 0° C. A 30% solution of hydrogen peroxide (3.1 mL, 27 mmol) was added dropwise and the reaction was stirred for 15 h allowing to warm to r.t. The reaction mixture was cooled to 0° C. and quenched by the addition of saturated sodium sulfite solution (50 mL). Extracted with dichloromethane (2×50 mL) and the combined organic layer were washed once with water, brine and dried over sodium sulfate. The solvent was removed under vacuum to obtain the crude product, which on purification by chromatography on SiO$_2$ column eluting with 10% ethyl acetate in hexane gave 4.62 g (89%) of required product 4 as an off white foam (alpha-beta mixture)

$^1$H NMR (δ, CDCl$_3$, 300 MHz): 0.62 (s, 3H), 0.83 (t, J=6 Hz, 3H), 2.28 (s, 3H), 3.92-3.98 (m, 4H), 5.85-5.91 (m, 1H).

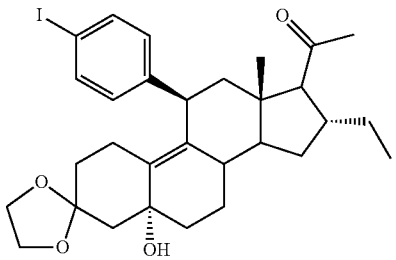 [SMILES: CC[C@@H]1CC2C3CC[C@@]4(O)CC5(CCC4=C3[C@@H](c3ccc(I)cc3)C[C@]2(C)C1C(C)=O)OCCO5]

3,3-Ethylenedioxy-16α-ethyl-5α-hydroxy-11-β-(4-iodo-phenyl)-19-norpregn-9-ene-20-one. (5)

A solution of 1,4-diiodobenzene (6.65 g, 20.18 mmol) in anhydrous THF (70 mL) was cooled to −15° C. as a 2M solution of isopropyl magnesium chloride in THF (10.09 mL, 20.18 mmol) was added dropwise over a period of 15 min keeping the temperature below −8° C. After stirring for 30 min, cuprous chloride (504.39 mg, 5.04 mmol) was added as a solid and the reaction mixture was stirred for 30 min. A solution of the epoxide 4 (3.9 g, 10.09 mmol) in 40 ml of THF was added dropwise and stirred for 2 h slowly warming to 10° C. The reaction was quenched with aqueous ammonium chloride solution (50 mL) and extracted with ethyl acetate (2×50 mL). The combined organic layer was washed further with water and brine, dried over sodium sulfate and evaporated in vacuo to afford crude product. The crude product was purified on a silica column eluting with 30% ethyl acetate in hexane to afford 4.6 g (78%) of 5 as an off white solid.

$^1$H NMR (δ, CDCl$_3$, 300 MHz): 0.32 (s, 3H), 0.82 (t, J=6 Hz, 3H), 2.2 (s, 3H), 3.88-3.99 (m, 4H), 4.31-4.33 (m, 1H), 6.91 (d, J=8.4 Hz, 2H), 7.57 (d, J=8.4 Hz, 2H).

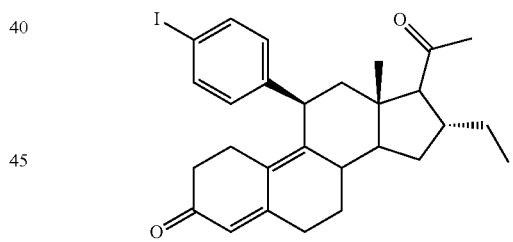

11β-{4'-iodophenyl}-16α-ethyl-19-norpregna-4,9-diene-3,20-dione. (6)

A solution of compound 5 (1.5 g, 2.54 mmol) in acetone (30 mL) at r.t was treated with aq. 2N hydrochloric acid solution (3.8 mL, 7.62 mmol). The reaction was quenched by the addition of saturated sodium bicarbonate solution after 10 min. Extracted with ethyl acetate (2×50 mL) and the combined organic layers were washed with water, brine and dried over an. sodium sulfate. The solvent was removed under vacuum to obtain the crude product which was purified on a silica column eluting with 30% ethyl acetate in hexane to give EC346 (3 g, 97%) as a white solid.

1H NMR (δ, CDCl3, 300 MHz): 0.32 (s, 3H), 0.82 (t, J=7.2 Hz, 3H), 1.27 (q, J=7.2 Hz, 2H), 2.15 (s, 3H), 4.32 (d, J=6.6 Hz, 1H), 5.78 (s, 1H), 6.91 (d, J=8.1 Hz, 2H), 7.58 (d, J=8.1 Hz, 2H).

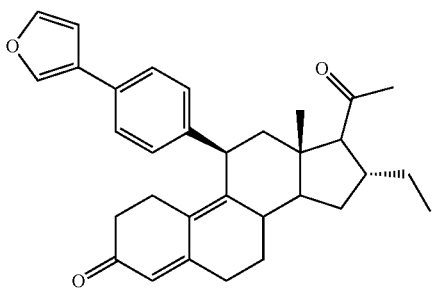 [SMILES: CC[C@@H]1CC2C3CCC4=CC(=O)CCC4=C3[C@@H](c3ccc(-c4ccoc4)cc3)C[C@]2(C)C1C(C)=O]

11β-{4'-[3'-furanyl)phenyl}-16α-ethyl-19-nor-pregna-4,9-diene-3,20-dione. (EC343)

A suspension of compound 7 (900 mg, 1.70 mmol), Furan-3-boronic acid (571 mg, 5.11 mmol), bis(triphenylphosphine)palladium(II) chloride (60 mg, 0.08 mmol), triphenyl arsine (63 mg, 0.2 mmol) and potassium carbonate (470 mg, 3.4 mmol) in dioxane (17 ml) and water (1.7 ml) was degassed three times using nitrogen-vacuum cycle. The reaction mixture was heated at reflux for 4 h, during which time TLC showed complete conversion of compound 7 to a more polar product. The reaction was quenched by the addition of water. Extracted with ethyl acetate (2×50 mL) and the combined organic layers were washed with water, brine and dried over an. sodium sulfate. The solvent was removed under vacuum to obtain the crude product which was purified on a silica column eluting with 50% ethyl acetate in hexane to give EC343 (3 g, 97%) as an off white solid.

1H NMR (δ, CDCl3, 300 MHz): 0.36 (s, 3H), 0.82 (t, J=6 Hz, 3H), 1.27 (q, J=6 Hz, 2H), 2.17 (s, 3H), 4.4 (d, J=6 Hz, 1H), 5.79 (s, 1H), 6.65-6.67 (m, 1H), 7.16 (d, J=8.1 Hz, 2H), 7.42 (d, J=8.1 Hz, 2H), 7.45-7.46 (m, 1H), 7.68-7.70 (m, 1H)

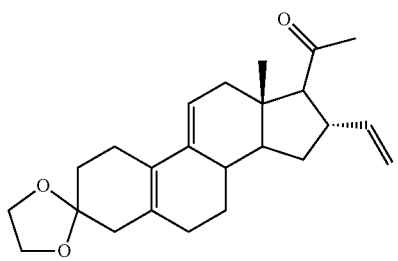 [SMILES: C=C[C@@H]1CC2C3CCC4=C(CCC5(C4)OCCO5)C3=CC[C@]2(C)C1C(C)=O]

3,3-Ethylenedioxy-16α-ethenyl-19-nor-pregna 5(10), 9(11)diene-20-one. (7)

A solution of Copper (II) acetate (203 mg, 1.45 mmol) in anhydrous THF (110 mL) was cooled to 0° C. as a 2M solution of vinyl magnesium bromide in THF (21 mL, 33.48 mmol) was added dropwise. A solution of compound 2 (3.8 g, 11.16 mmol) together with chlorotrimethyl silane (6.06 g, 55 mmol) in THF (40 mL) was added dropwise keeping the temperature below 1° C. After an hour at 0° C., 7 mL of vinyl magnesium bromide was added and the reaction was stirred for 30 min. The reaction was quenched by the addition of saturated ammonium chloride solution (50 mL). Extracted with ethyl acetate (3×50 mL) and the combined organic layer were washed once with water, brine and dried over sodium sulfate. The solvent was removed under vacuum to obtain the crude product, which on purification by chromatography on SiO$_2$ column eluting with 15% ethyl acetate in hexane gave 3.80 g (92%) of required product 7 as a pale yellow solid.

$^1$H NMR (δ, CDCl$_3$, 300 MHz): 0.62 (s, 3H), 2.13 (s, 3H), 3.23-3.34 (m, 1H), 3.98 (s, 4H), 4.84-4.98 (m, 2H), 5.53-5.55 (m, 1H), 5.68-5.79 (m, 1H).

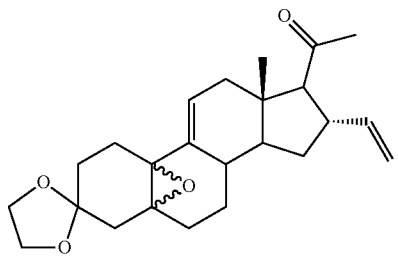

3,3-Ethylenedioxy-16α-ethenyl-5,10-epoxy-19-nor-pregn-9(11)-ene-20-one. (8)

To a solution of compound 7 (3.8 g, 10.3 mmol) in dichloromethane (40 ml) was added hexafluoroacetone trihydrate (2.74 g, 12.37 mmol) and Na$_2$HPO$_4$ (1.6 g, 11.33 mmol). This suspension was vigorously stirred and cooled to 0° C. A 30% solution of hydrogen peroxide (2.3 mL, 20.6 mmol) was added dropwise and the reaction was stirred for 15 h allowing to warm to r.t. The reaction mixture was cooled to 0° C. and quenched by the addition of saturated sodium sulfite solution (50 mL). Extracted with dichloromethane (2×50 mL) and the combined organic layer were washed once with water, brine and dried over sodium sulfate. The solvent was removed under vacuum to obtain the crude product, which on purification by chromatography on SiO$_2$ column eluting with 10% ethyl acetate in hexane gave 3.3 g (82%) of required product 8 as an off white foam (alpha-beta mixture)

$^1$H NMR (δ, CDCl$_3$, 300 MHz): 0.67 (s, 3H), 2.14 (s, 3H), 3.21-3.32 (m, 1H), 3.87-3.97 (m, 4H), 4.85-4.97 (m, 2H), 5.65-5.77 (m, 1H), 6.02-6.04 (m, 1H)

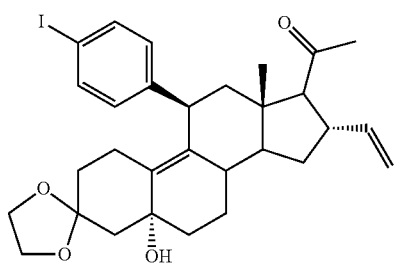 [SMILES: C=C[C@@H]1CC2C3CC[C@@]4(O)CC5(CCC4=C3[C@@H](c3ccc(I)cc3)C[C@]2(C)C1C(C)=O)OCCO5]

3,3-Ethylenedioxy-16α-ethenyl-5α-hydroxy-11-β-(4-iodo-phenyl)-19-norpregn-9-ene-20-one. (9)

A solution of 1,4-diiodobenzene (4.97 g, 15.08 mmol) in anhydrous THF (50 mL) was cooled to −15° C. as a 2M solution of isopropyl magnesium chloride in THF (7.54 mL, 15.08 mmol) was added dropwise over a period of 15 min keeping the temperature below −8° C. After stirring for 30 min, cuprous chloride (375 mg, 3.75 mmol) was added as a solid and the reaction mixture was stirred for 30 min. A solution of the epoxide 8 (2.9 g, 7.5 mmol) in 30 ml of THF was added dropwise and stirred for 2 h slowly warming to 10° C. The reaction was quenched with aqueous ammonium chloride solution (50 mL) and extracted with ethyl acetate (2×50 mL). The combined organic layer was washed further with water and brine, dried over sodium sulfate and evaporated in vacuo to afford crude product. The crude product was purified on a silica column eluting with 30% ethyl acetate in hexane to afford 3.11 g (70%) of 9 as an off white solid.

$^1$H NMR (δ, CDCl$_3$, 300 MHz): 0.31 (s, 3H), 2.12 (s, 3H), 3.15-3.20 (m, 1H), 3.88-4.03 (m, 4H), 4.23 (d, J=7.3 Hz, 1H), 4.37 (s, 1H), 4.82-4.96 (m, 2H), 5.62-5.74 (m, 1H), 6.95 (d, J=8.4 Hz, 2H), 7.55 (d, J=8.4 Hz, 2H).

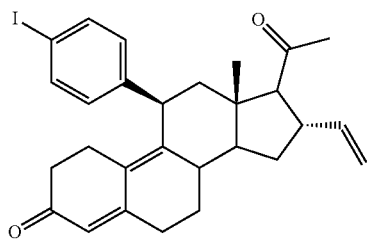 [SMILES: C=C[C@@H]1CC2C3CCC4=CC(=O)CCC4=C3[C@@H](c3ccc(I)cc3)C[C@]2(C)C1C(C)=O]

11β-{4'-iodophenyl}-16α-ethenyl-19-norpregna-4,9-diene-3,20-dione. (10)

A solution of compound 9 (1.5 g, 2.5 mmol) in acetone (20 mL) at r.t was treated with aq. 2N hydrochloric acid solution (3.75 mL, 7.5 mmol). The reaction was quenched by the addition of saturated sodium bicarbonate solution after 10 min. Extracted with ethyl acetate (2×50 mL) and the combined organic layers were washed with water, brine and dried over an. sodium sulfate. The solvent was removed under vacuum to obtain the crude product which was purified on a silica column eluting with 30% ethyl acetate in hexane to give compound 10 (1.06 g, 81%) as a white solid.

$^1$H NMR (δ, CDCl$_3$, 300 MHz): 0.37 (s, 3H), 2.14 (s, 3H), 3.16-3.30 (m, 1H), 4.34 (d, J=6 Hz, 1H), 4.86-4.97 (m, 2H), 5.65-5.74 (m, 1H), 5.78 (s, 1H), 6.92 (d, J=8.2 Hz, 2H), 7.58 (d, J=8.4 Hz, 2H).

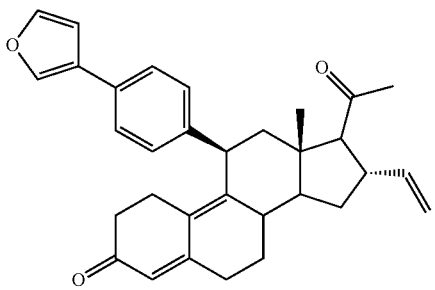 [SMILES: C=C[C@@H]1CC2C3CCC4=CC(=O)CCC4=C3[C@@H](c3ccc(-c4ccoc4)cc3)C[C@]2(C)C1C(C)=O]

11β-{4'-[3'-furanyl)phenyl}-16α-ethenyl-19-norpregna-4,9-diene-3,20-dione. (EC345)

A suspension of compound 10 (1.15, 2.18 mmol), Furan-3-boronic acid (733.2 mg, 6.55 mmol), bis(triphenylphosphine)palladium(II) chloride (77 mg, 0.11 mmol), triphenyl arsine (80.11 mg, 0.26 mmol) and potassium carbonate (602 mg, 4.36 mmol) in dioxane (22 ml) and water (2.2 ml) was degassed three times using nitrogen-vacuum cycle. The reaction mixture was heated at reflux for 4 h, during which time TLC showed complete conversion of compound 10 to a more polar product. The reaction was quenched by the addition of water. Extracted with ethyl acetate (3×50 mL) and the combined organic layers were washed with water, brine and dried over an. sodium sulfate. The solvent was removed under vacuum to obtain the crude product which was purified on a silica column eluting with 50% ethyl acetate in hexane to give EC345 (600 mg, 59%) as an off white solid.

1H NMR (δ, CDCl3, 300 MHz): 0.39 (s, 3H), 2.15 (s, 3H), 3.20-3.27 (m, 1H), 4.41 (d, J=6 Hz, 1H), 4.86-4.96 (m, 2H), 5.69-5.75 (m, 1H), 5.78 (s, 1H), 6.60-6.66 (m, 1H), 7.16 (d, J=8.1 Hz, 2H), 7.39 (d, J=8.1 Hz, 2H), 7.45-7.46 (m, 1H), 7.69-7.71 (m, 1H)

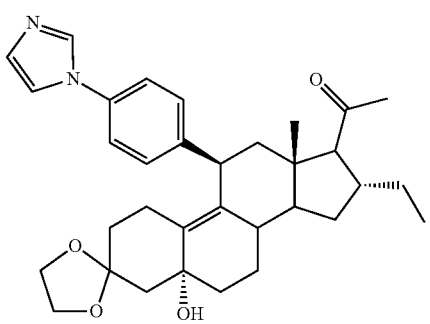 [SMILES: CC[C@@H]1CC2C3CC[C@@]4(O)CC5(CCC4=C3[C@@H](c3ccc(-n4ccnc4)cc3)C[C@]2(C)C1C(C)=O)OCCO5]

3,3-Ethylenedioxy-16α-ethyl-5α-hydroxy-11β-{4'-[1' imidazolyl)phenyl}-19-norpregn-9-ene-20-one (11)

A mixture of compound 5 (4.6 g, 7.8 mmol), imidazole (583 mg, 8.56 mmol), cuprous iodide (149 mg, 0.78 mmol), N, N-dimethyl glycine (161 mg, 1.56 mmol) and potassium carbonate (2.15 g, 15.6 mmol) in anhydrous DMSO (10 mL) was degassed three times applying vacuum and nitrogen and was immersed in to a preheated oil bath at 110° C. The reaction mixture was heated for 60 h. After cooling to room temperature, the reaction mixture was diluted with ethyl acetate (200 mL) and filtered through a Celite pad. The filtrate was transferred to a separatory funnel and was washed with water, brine and dried over anhydrous sodium sulfate. The solvent was removed under vacuum to afford the crude product, which on purification by chromatography on SiO$_2$ column eluting with 5% isopropanol in dichloromethane with 1% ammonium hydroxide as an additive gave 3.6 g (87%) of required product 11 as an off white amorphous solid.

$^1$H NMR (δ, CDCl$_3$, 300 MHz): 0.29 (s, 3H), 0.80 (t, J=6 Hz, 3H), 2.18 (s, 3H), 3.90-4.02 (m, 4H), 4.33 (d, J=6.9 Hz, 1H), 4.38 (br s, —OH), 7.27-7.31 (m, 7H)

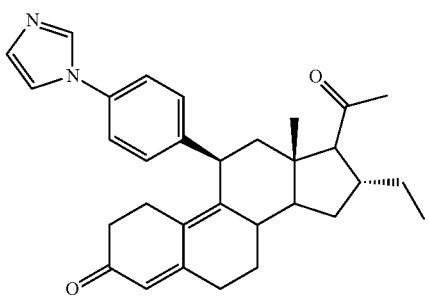 [SMILES: CC[C@@H]1CC2C3CCC4=CC(=O)CCC4=C3[C@@H](c3ccc(-n4ccnc4)cc3)C[C@]2(C)C1C(C)=O]

11β-{4'-[1' imidazolyl)phenyl}-16α-ethyl-19-nor-pregna-4,9-diene-3,20-dione. (EC346)

A solution of compound 6 (3.6 g, 6.78 mmol) in acetone (40 mL) at r.t was treated with aq. 2N hydrochloric acid solution (10.17 mL, 20.35 mmol). The reaction was quenched by the addition of saturated sodium bicarbonate solution after 10 min. Extracted with ethyl acetate (3×50 mL) and the combined organic layers were washed with water, brine and dried over an. sodium sulfate. The solvent was removed under vacuum to obtain the crude product which was purified on a silica column eluting with 5% isopropanol in methylene chloride to give EC346 (3 g, 97%) as a pale yellow solid.

$^1$H NMR (δ, CDCl$_3$, 300 MHz): 0.36 (s, 3H), 0.83 (t, J=6 Hz, 3H), 2.18 (s, 3H), 4.44 (d, J=6.6 Hz, 1H), 5.8 (s, 1H), 7.12-7.31 (m, 6H), 7.8 (s, 1H).

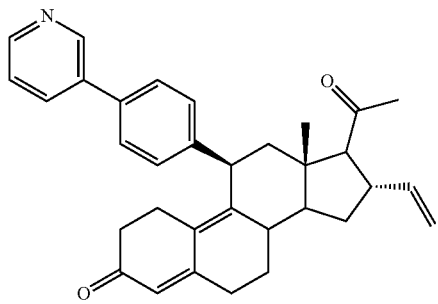 [SMILES: C=C[C@@H]1CC2C3CCC4=CC(=O)CCC4=C3[C@@H](c3ccc(-c4cccnc4)cc3)C[C@]2(C)C1C(C)=O]

11β-{4'-[3'-pyridinyl)phenyl}-16α-ethenyl-19-nor-pregna-4,9-diene-3,20-dione. (EC344)

A suspension of compound 11 (1.06 g, 2 mmol), Pyridine-3-boronic acid (742.5 mg, 6.04 mmol), bis(triphenylphosphine)palladium(II) chloride (71 mg, 0.1 mmol), triphenyl arsine (74 mg, 0.24 mmol) and potassium carbonate (417 mg, 3.02 mmol) in dioxane (15 ml) and water (1.5 ml) was degassed three times using nitrogen-vacuum cycle. The reaction mixture was heated at reflux for 4 h, during which time TLC showed complete conversion of compound 11 to a more polar product. The reaction was quenched by the addition of water. Extracted with ethyl acetate (3×50 mL) and the combined organic layers were washed with water, brine and dried over an. sodium sulfate. The solvent was removed under vacuum to obtain the crude product which was purified on a silica column eluting with 50% ethyl acetate in hexane to give EC344 (690 mg, 72%) as an off white solid.

1H NMR (δ, CDCl3, 300 MHz): 0.41 (s, 3H), 2.17 (s, 3H), 3.2-3.27 (m, 1H), 4.47 (d, J=6 Hz, 1H), 4.87-4.98 (m, 2H), 5.67-5.76 (m, 1H), 5.80 (s, 1H), 7.28 (d, J=8.2 Hz, 2H), 7.34-7.38 (m, 1H), 7.51 (d, J=8.1 Hz, 2H), 7.85 (d, J=7.8 Hz, 1H), (m, 1H), 8.57 (s, 1H), 8.83 (s, 1H).

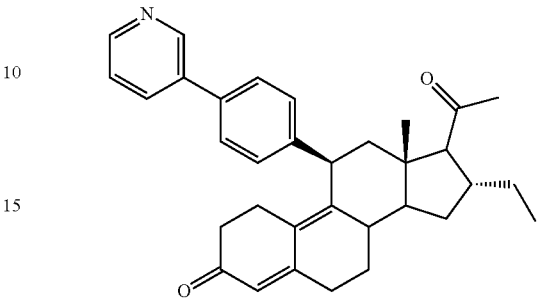

11β-{4'-[3'-pyridinyl)phenyl}-16α-ethyl-19-nor-pregna-4,9-diene-3,20-dione. (EC342)

A suspension of compound 6 (600 mg, 1.13 mmol), Pyridine-3-boronic acid (417 mg, 3.4 mmol), bis(triphenylphosphine)palladium(II) chloride (40 mg, 0.05 mmol), triphenyl arsine (41 mg, 0.13 mmol) and potassium carbonate (234 mg, 1.7 mmol) in dioxane (12 ml) and water (1.2 ml) was degassed three times using nitrogen-vacuum cycle. The reaction mixture was heated at reflux for 4 h, during which time TLC showed complete conversion of compound 6 to a more polar product. The reaction was quenched by the addition of water. Extracted with ethyl acetate (3×50 mL) and the combined organic layers were washed with water, brine and dried over an. sodium sulfate. The solvent was removed under vacuum to obtain the crude product which was purified on a silica column eluting with 50% ethyl acetate in hexane to give EC344 (440 mg, 81%) as an off white solid.

$^1$H NMR (δ, CDCl3, 300 MHz): 0.37 (s, 3H), 0.83 (t, J=6 Hz, 3H), 2.19 (s, 3H), 4.46 (d, J=6.9 Hz, 1H), 5.8 (s, 1H), 7.27 (d, J=8.2 Hz, 2H), 7.35-7.38 (m, 1H), 7.5 (d, J=8.2 Hz, 2H), 7.83-7.87 (m, 1H), 8.56-8.59 (m, 1H), 8.83 (s, 1H).

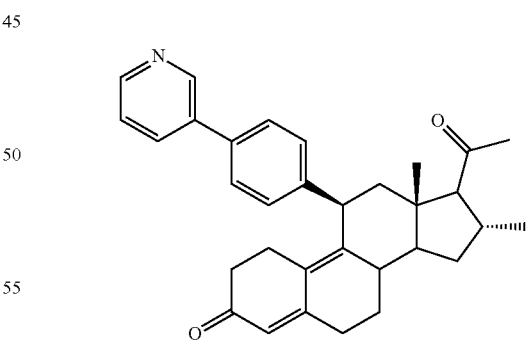

11β-{4'-[3'-pyridinyl)phenyl}-16α-methyl-19-nor-pregna-4,9-diene-3,20-dione. (EC348)

A suspension of compound 15 (670 mg, 1.3 mmol), Pyridine-3-boronic acid (480 mg, 3.9 mmol), bis(triphenylphosphine)palladium(II) chloride (46 mg, 0.06 mmol), triphenyl arsine (48 mg, 0.16 mmol) and potassium carbonate (270 mg, 1.95 mmol) in dioxane (15 ml) and water (1.5 ml)

was degassed three times using nitrogen-vacuum cycle. The reaction mixture was heated at reflux for 4 h, during which time TLC showed complete conversion of compound 15 to a more polar product. The reaction was quenched by the addition of water. Extracted with ethyl acetate (3×50 mL) and the combined organic layers were washed with water, brine and dried over an. sodium sulfate. The solvent was removed under vacuum to obtain the crude product which was purified on a silica column eluting with 50% ethyl acetate in hexane to give EC348 (480 mg, 79%) as an off white solid.

¹H NMR (δ, CDCl3, 300 MHz): 0.37 (s, 3H), 0.98 (d, J=6 Hz, 3H), 2.19 (s, 3H), 4.46 (d, J=6.9 Hz, 1H), 5.8 (s, 1H), 7.27 (d, J=8.2 Hz, 2H), 7.33-7.37 (m, 1H), 7.51 (d, J=8.2 Hz, 2H), 7.83-7.89 (m, 1H), 8.56-8.59 (m, 1H), 8.83 (s, 1H).

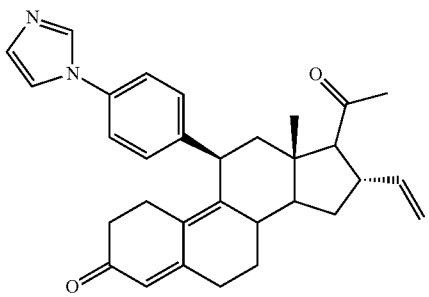 [SMILES: C=C[C@@H]1CC2C3CCC4=CC(=O)CCC4=C3[C@@H](c3ccc(-n4ccnc4)cc3)C[C@]2(C)C1C(C)=O]

A mixture of compound 9 (2.2 g, 3.73 mmol), imidazole (280 mg, 4.1 mmol), cuprous iodide (71 mg, 0.37 mmol), N,N-dimethyl glycine (77 mg, 0.75 mmol) and potassium carbonate (1.03 g, 7.46 mmol) in anhydrous DMSO (10 mL) was degassed three times applying vacuum and nitrogen and was immersed in to a preheated oil bath at 110° C. The reaction mixture was heated for 60 h. After cooling to room temperature, the reaction mixture was diluted with ethyl acetate (200 mL) and filtered through a Celite pad. The filtrate was transferred to a separatory funnel and was washed with water, brine and dried over anhydrous sodium sulfate. The solvent was removed under vacuum to afford the crude product 16, which was hydrolyzed using 4N HCl (3.4 ml, 6.8 mmol) to afford crude EC-347. Purification of the crude by chromatography on $SiO_2$ column eluting with 5% isopropanol in dichloromethane with 1% ammonium hydroxide as an additive gave 1 g (63%) of EC-347 as a pale yellow amorphous solid.

¹H NMR (δ, CDCl3, 300 MHz): 0.40 (s, 3H), 2.17 (s, 3H), 3.2-3.27 (m, 1H), 4.46 (d, J=6 Hz, 1H), 4.88-4.98 (m, 2H), 5.68-5.76 (m, 1H), 5.81 (s, 1H), 7.2-7.34 (m, 6H), 7.84 (s, 1H).

The following biological tests were performed with the test compounds.

Transactivation Assay for Progesterone Agonist and Antagonistic Activity (See Table 1).

Experimental: PR transactivation studies was carried out in human breast cancer (T47D) cells, grown in RPMI medium without phenol red and 5% charcoal stripped fetal bovine serum, transiently transfected with PR luciferase reporter (CCS-6043L signal reporter assay kit, Qiagen). The cells were stimulated R5020 as PR agonist and treated in the presence or absence of the tested compounds for 24 hours. The effect was calculated using dual luciferase assay kit (Promega, WI)) based on RU486 as full antagonist and R5020 as agonist for progesterone receptor.

TABLE 1

| S: No | Cell Line Tested | Stimulant | IC50 Average of 2 expts (nM) | Control Cmpd Name | Control IC50 (nM) | Antagonist rel to RU486 (%) | Cmpd Name |
|---|---|---|---|---|---|---|---|
| 1 | T47D | R5020 | 0.7 | RU-486 | 1.2 | 300 | CDB-4124 |
| 2 | T47D | R5020 | 0.65 | RU-486 | 1.2 | 120 | CDB-2914 |
| 3 | T47D | R5020 | 0.325 | RU-486 | 1.2 | 342.9 | BAY |
| 4 | T47D | R5020 | 0.46 | RU-486 | 1.2 | 255.3 | EC-317 |
| 5 | T47D | R5020 | 0.625 | RU-486 | 1.2 | 160 | EC-312 |
| 6 | T47D | R5020 | 0.5 | RU-486 | 1.2 | 240 | EC-313 |
| 7 | T47D | R5020 | 0.62 | RU-486 | 1.2 | 193.5 | ASOPRISNIL |
| 8 | T47D | R5020 | 0.45 | RU-486 | 1.2 | 266.7 | J912 |
| 9 | T47D | R5020 | 0.95 | RU-486 | 1.2 | 120 | EC-342 |
| 10 | T47D | R5020 | 2.1 | RU-486 | 1.2 | 57.1 | EC343 |
| 11 | T47D | R5020 | 0.95 | RU-486 | 1.2 | 120 | EC347 |
| 12 | T47D | R5020 | 5 | RU-486 | 1.2 | 21.8 | EC336 |
| 13 | T47D | R5020 | 0.39 | RU-486 | 1.2 | 292.7 | EC348 |
| 14 | T47D | R5020 | 0.35 | RU-486 | 1.2 | 324 | EC344 |
| 15 | T47D | R5020 | 1.0 | RU-486 | 1.2 | 120 | EC345 |
| 16 | T47D | R5020 | 0.3 | RU-486 | 1.2 | 378 | EC346 |

| S: No | Cell Line Tested | Stimulant | EC50 (nM) | Control Cmpd Name | Control EC50 (nM) | Agonist rel to R5020 (%) | Cmpd Name |
|---|---|---|---|---|---|---|---|
| 1 | T47D | R5020 | 21.5 | R5020 | 0.35 | 1.5 | CDB2914 |
| 2 | T47D | R5020 | 25 | R5020 | 0.35 | 1.4 | CDB4124 |
| 3 | T47D | R5020 | 9.5 | R5020 | 0.35 | 3.9 | BAY 1002670 |
| 4 | T47D | R5020 | 100 | R5020 | 0.35 | 0.35 | EC317 |
| 5 | T47D | R5020 | 51.5 | R5020 | 0.35 | 0.73 | EC312 |
| 6 | T47D | R5020 | 4.75 | R5020 | 0.35 | 7.8 | EC313 |
| 7 | T47D | R5020 | 4.9 | R5020 | 0.35 | 7.14 | ASOPRISNIL |
| 8 | T47D | R5020 | 7.5 | R5020 | 0.35 | 4.67 | J912 |
| 9 | T47D | R5020 | 5.15 | R5020 | 0.35 | 7 | EC342 |
| 10 | T47D | R5020 | 4.75 | R5020 | 0.35 | 6.4 | EC343 |
| 11 | T47D | R5020 | 3.4 | R5020 | 0.35 | 9.7 | EC347 |
| 12 | T47D | R5020 | 5 | R5020 | 0.35 | 7 | EC336 |

TABLE 1-continued

| 13 | T47D | R5020 | 4.61 | R5020 | 0.35 | 7.0 | EC348 |
| 14 | T47D | R5020 | 100 | R5020 | 0.35 | 0.32 | EC344 |
| 15 | T47D | R5020 | 49 | R5020 | 0.35 | 0.65 | EC345 |
| 16 | T47D | R5020 | 100 | R5020 | 0.35 | 0.32 | EC346 |

TABLE 2

| S: No | Cmpd Name | PR agonism (IC50) | PR antagonism (IC50) | Ratio of IC50's |
|---|---|---|---|---|
| 1 | CDB4124 | 21.5 | 0.7 | 30.7 |
| 2 | CDB2914 | 25 | 0.65 | 38.4 |
| 3 | BAY 1002670 | 9.5 | 0.33 | 28.7 |
| 4 | EC317 | 100 | 0.46 | 217.3 |
| 5 | EC312 | 51.5 | 0.63 | 81.7 |
| 6 | EC313 | 4.7 | 0.5 | 9.4 |
| 7 | ASOPRISNIL | 4.9 | 0.62 | 7.9 |
| 8 | J912 | 7.5 | 0.45 | 16.6 |
| 9 | EC342 | 5.15 | 0.95 | 5.7 |
| 10 | EC343 | 4.75 | 2.1 | 2.2 |
| 11 | EC347 | 3.4 | 0.95 | 3.5 |
| 12 | EC336 | 5 | 5 | 1.0 |
| 13 | EC348 | 4.61 | 0.39 | 11.8 |

Figure 1B:
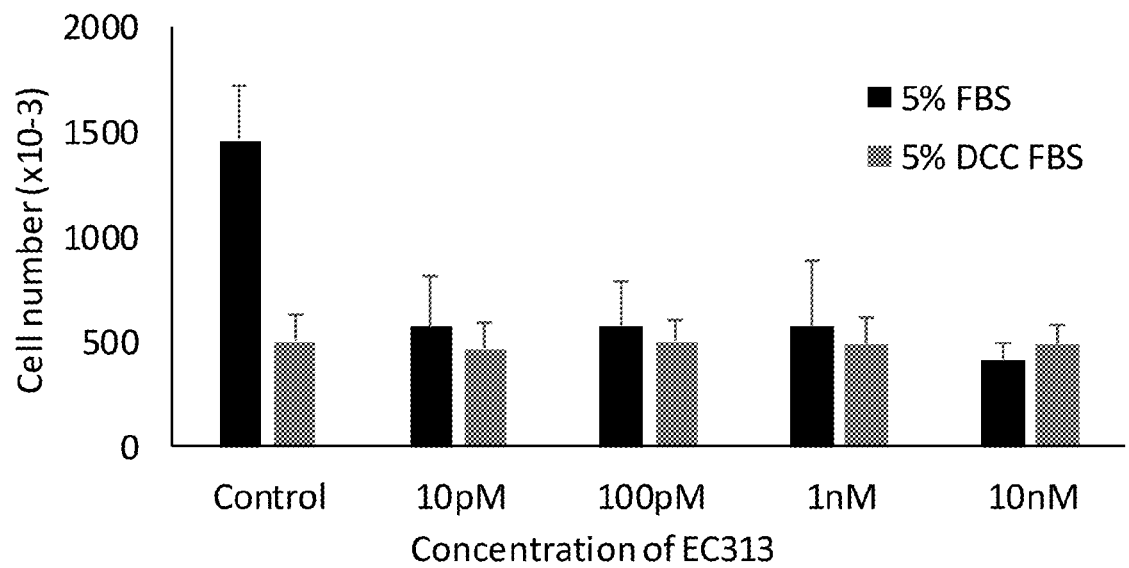
Figure 1C:
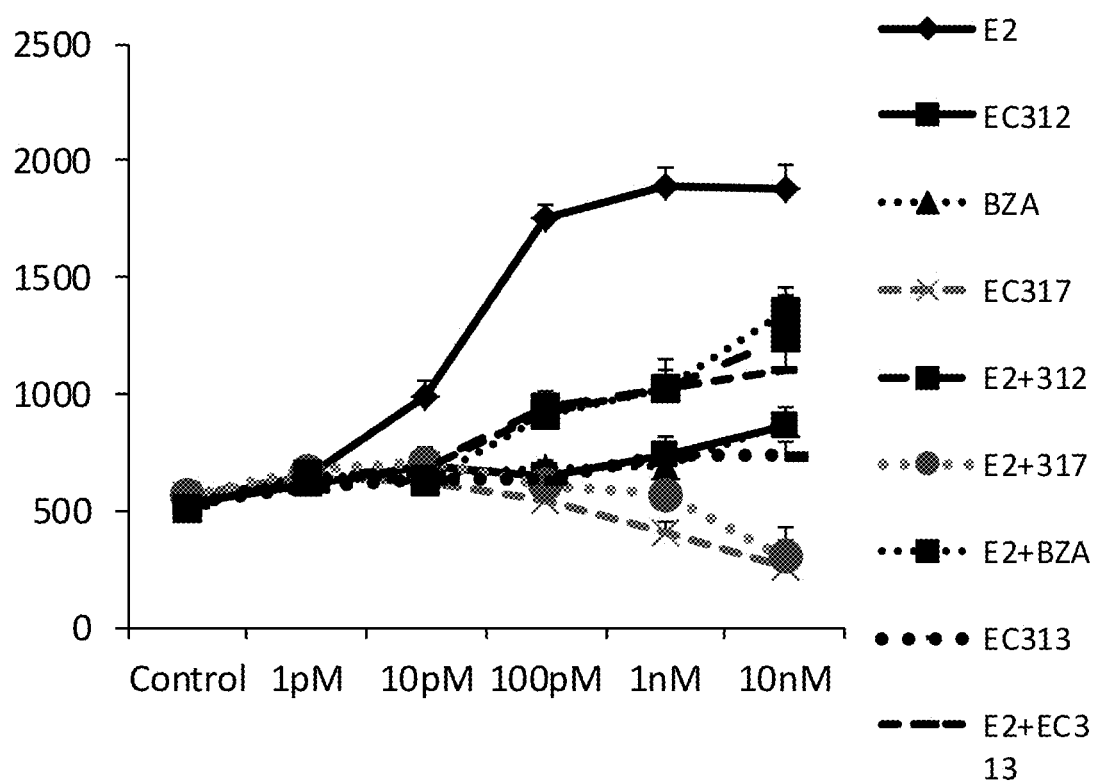
FIG. 1C depicts compounds treated as per the conditions in FIGS. 1A and 1B with and without E2 (0.1 nM)
Figure 2A:
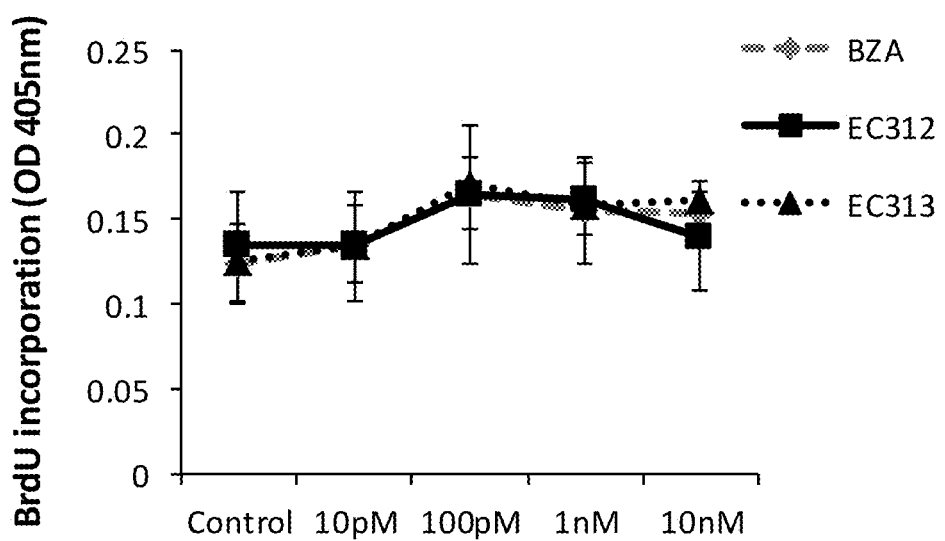
FIGS. 2A-2B depicts the effect of EC312 and EC313 on cell proliferation as assessed by BrdU incorporation.
Figure 2B:
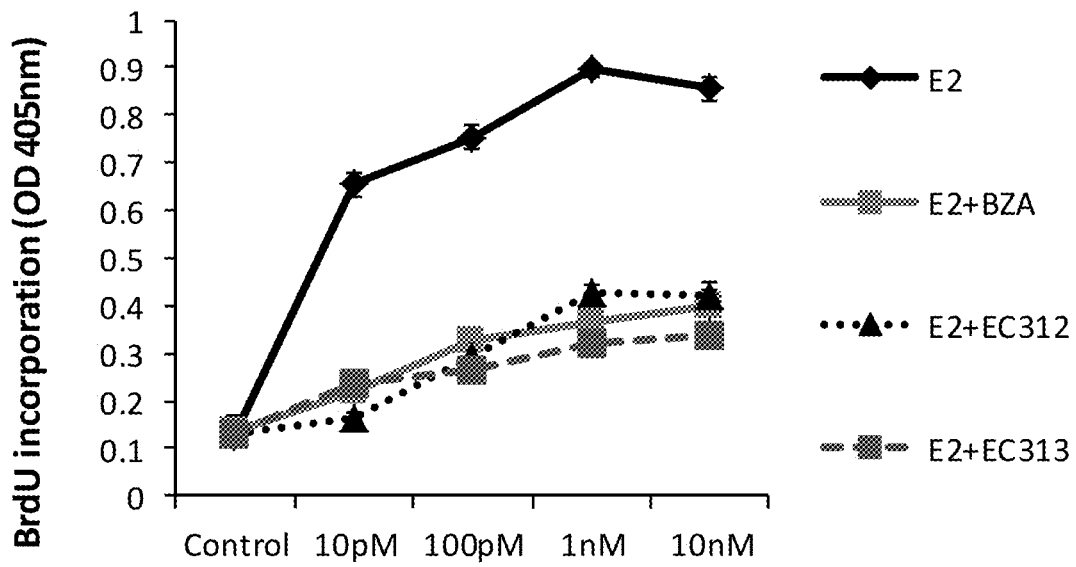
Figure 2C:
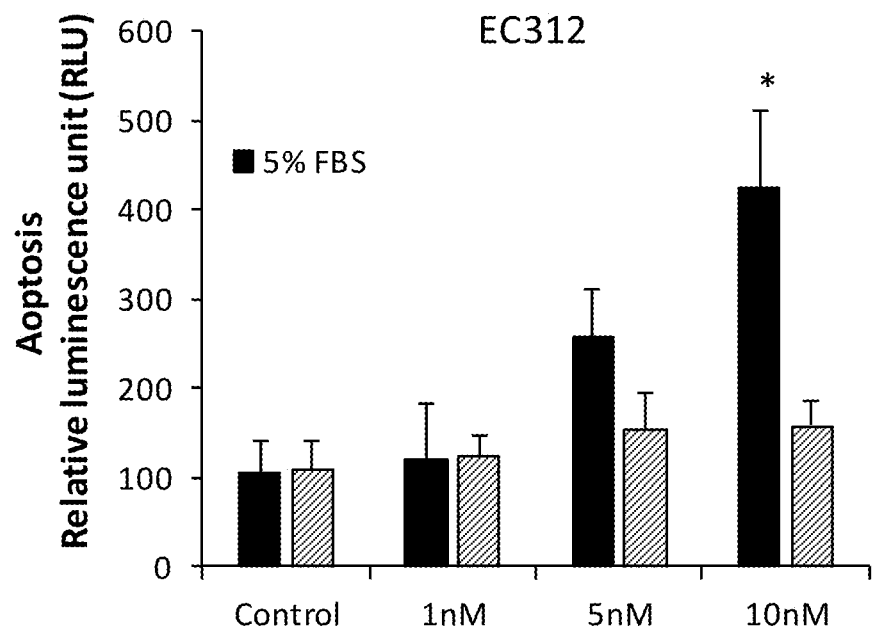
FIGS. 2C-2D depict the effect of EC312 and EC313 on apoptosis under the conditions of presence and absence of endogenous estrogen.
Figure 2D:
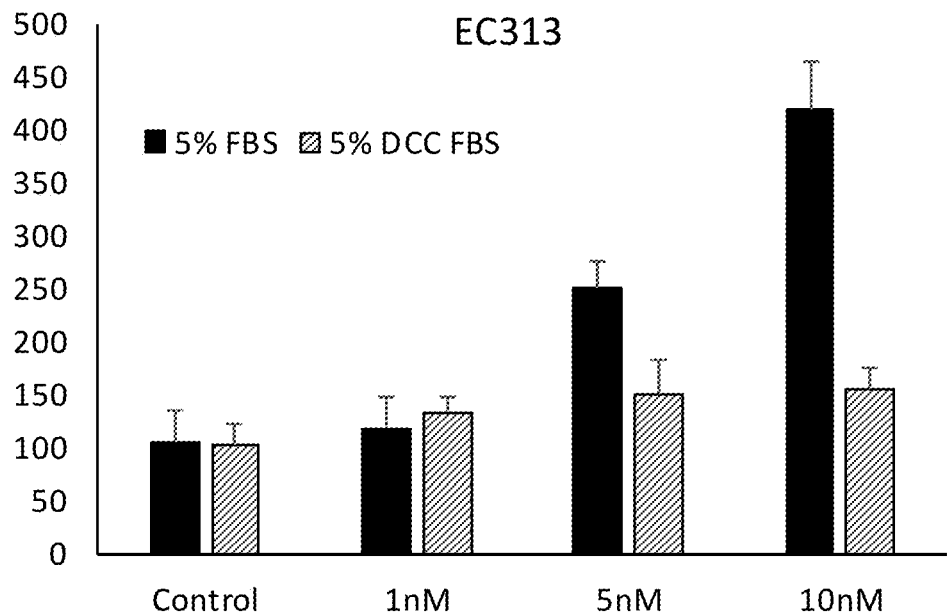
Figure 3A:
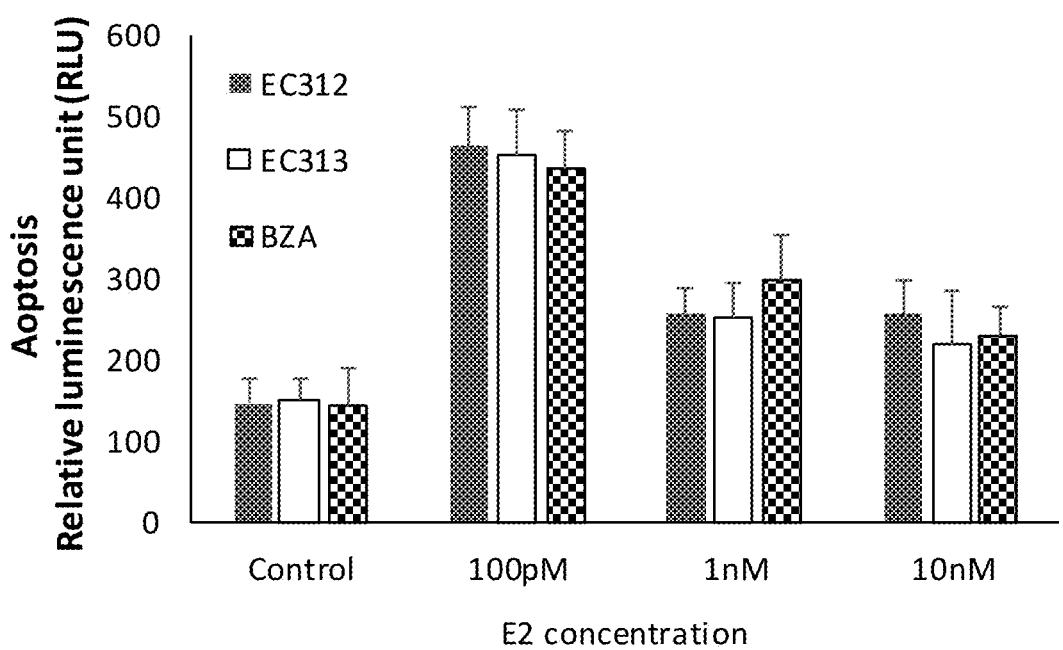
FIG. 3A depicts the effect of EC312 and EC313 on apoptosis in the absence of endogenous estrogen and increasing concentrations of exogenous E2.
Figure 3B:
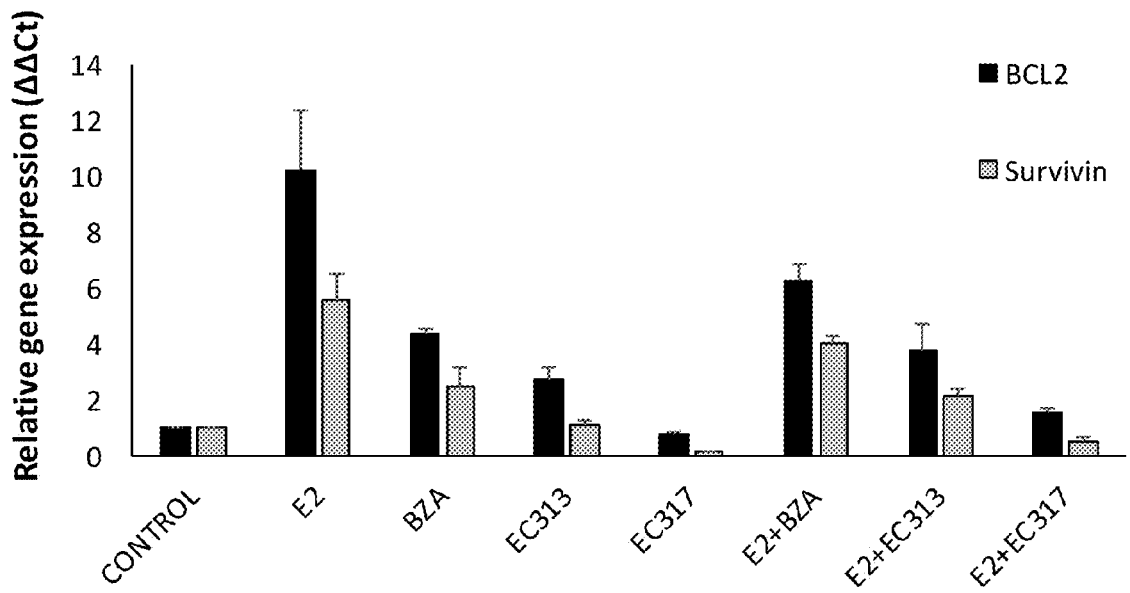
FIGS. 3B-3C depict gene expression of T47D cells in response to EC312 and EC313 for anti and pro-apoptotic genes.
Figure 3C:
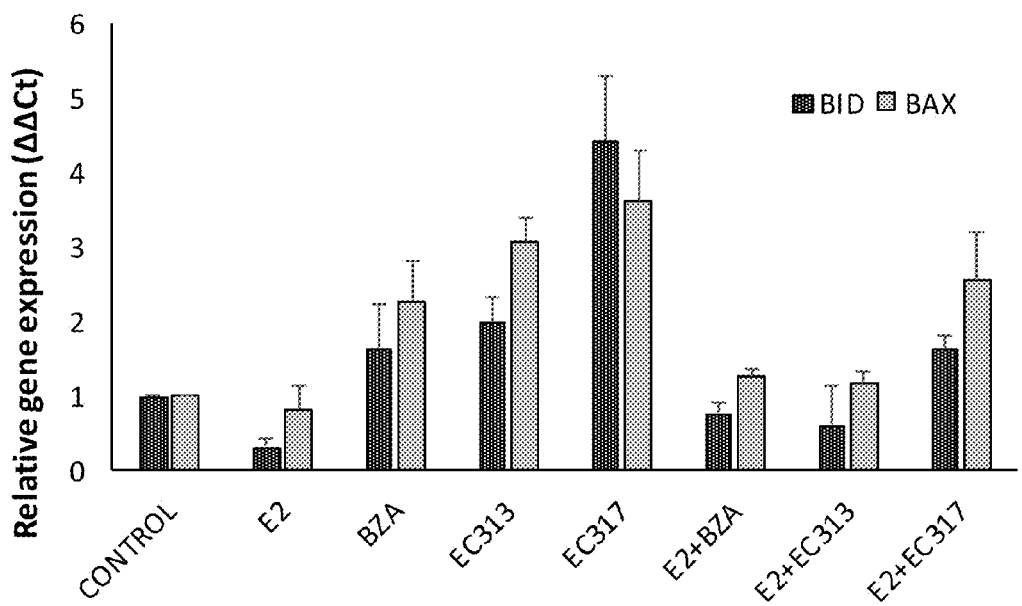
Figure 3D:
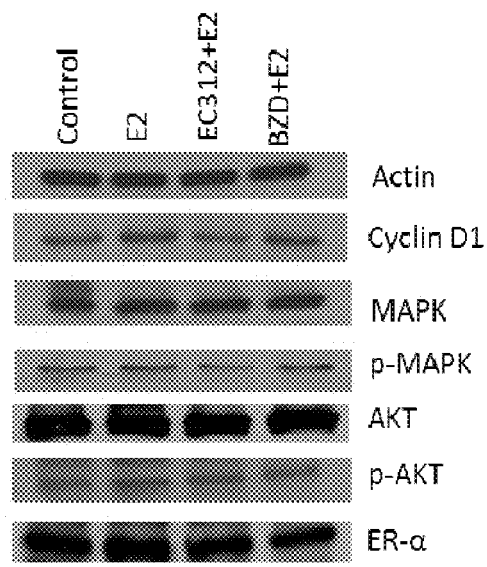
FIG. 3D depicts the effect of EC312 and BZA on the expression of ER, Cyclin D1 and phosphorylation of MAPK and AKT.
Figure 4A:
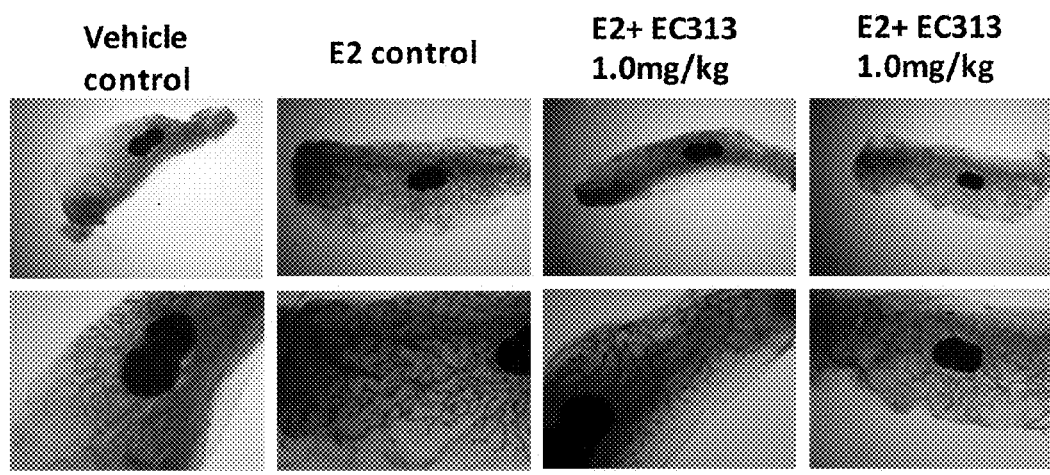
FIG. 4A depicts whole mounts of mammary glands of overictomized C57BL/6 mice treated with E2, EC313 0.1 and 1.0 mg/kg.
Figure 4B:
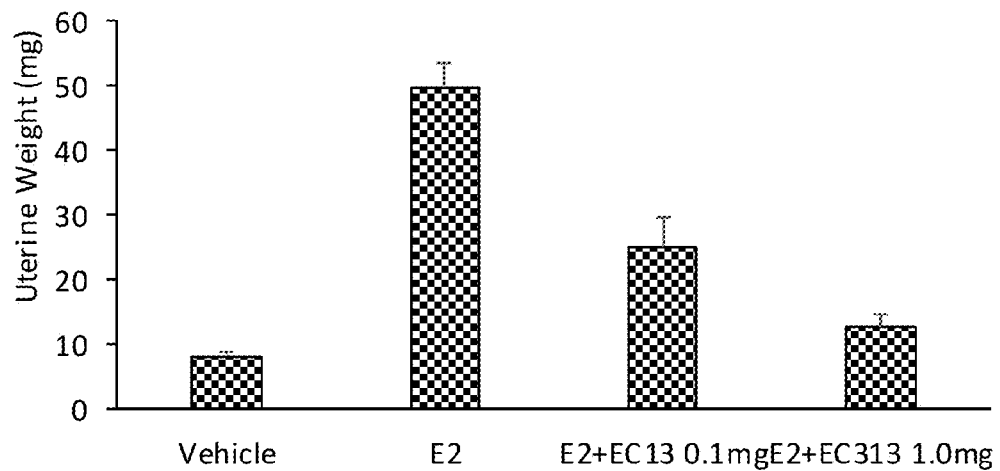
FIG. 4B depicts uterine weight of mice treated for 4 weeks with E2, EC313 0.1 and 1.0 mg/kg.
Figure 4C:
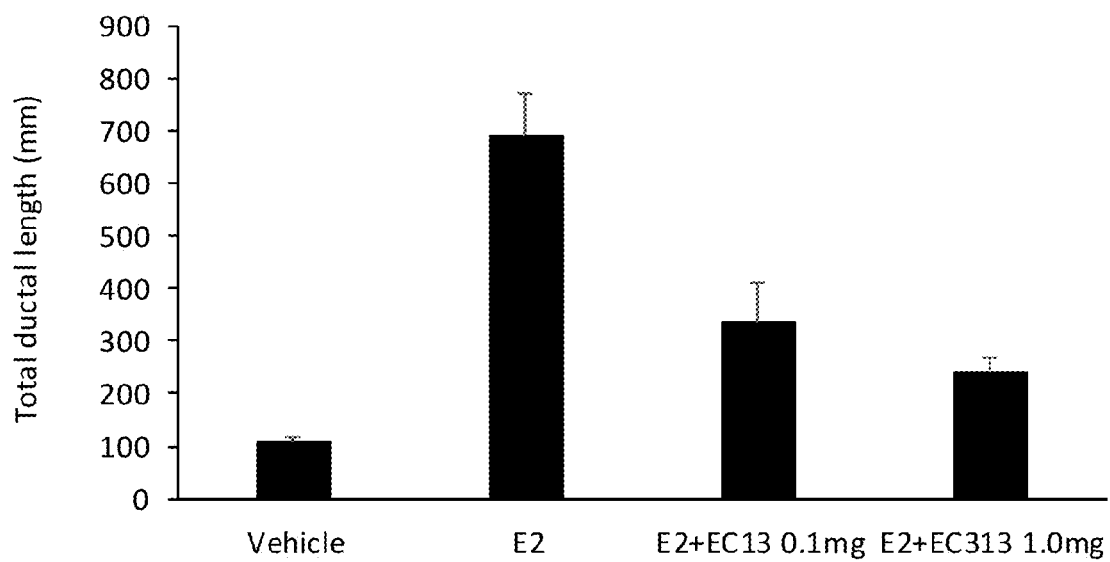
FIGS. 4C-4D depict total duct length and terminal end bud counts in the mammary gland whole mounts after 4 weeks of the treatment with test compounds (*P<0.001 vs E2-control)
Figure 4D:
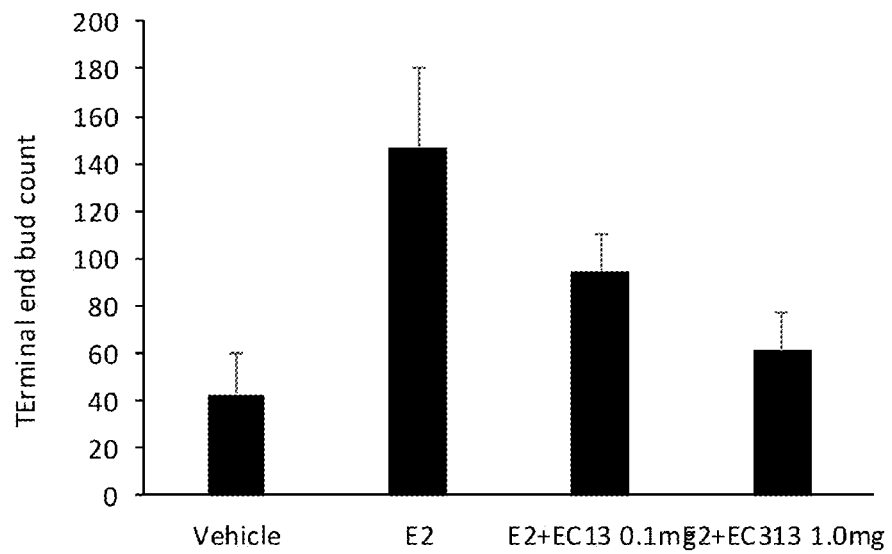

Antiestrogenic Effect of EC312 and EC313 on Cell Growth in the Presence and Absence of Endogenous Estrogens in T47D Cells (See FIG. 1)

FIG. 1. A-B,

Antiestrogenic effect of EC312 and EC313 on cell growth in the presence and absence of endogenous estrogens. T47D cells were plated at 30,000 cells per well in 5% FBS-RPMI and grown for 2 days before treatment. The cells were then incubated with EC312 and EC313 at indicated concentrations for 5 days and counted for cell number. *P<0.01 vs control. C, The compounds were treated as per the conditions above with and without E2 (0.1 nM). Tested compounds were found to inhibit E2 induced cell proliferation as comparable to that of BZA. EC317 was used as a pure PR antagonist (*P<0.01 vs control).

FIG. 2. A-B,

Effect of EC312 and EC313 on cell proliferation as assessed by BrdU incorporation. T47D cells were plated in 96-well plates at a density of 10,000 cells per well. Two days later the culture medium (5% FCS-RPMI) was replaced with phenol red-free RPMI with 5% DCC-FCS. After 24 hours of starvation, the cells were treated with increasing doses of the compounds alone or in combination with E2 (0.1 nM). The results are expressed as average OD value of quadruplicate wells (*P<0.01 vs control). C-D, Effect of EC312 and EC313 on apoptosis under the conditions of presence and absence of endogenous estrogen. T47D cells were plated in 12 well plated at a density of 80,000 cells/well. Two days later culture media were replaced with phenol red-free RPMI containing 5% FBS or 5% DCC-FBS. After 24 hours of starvation, cells were treated with test compounds at increasing concentrations for 48 hours. Apoptosis was assessed by Caspase-Glo assay kit (Promega). The results were expressed as OD±SEM of 2 wells per treatment (*P<0.01 vs control).

FIG. 3. A,

Effect of EC312 and EC313 on apoptosis in the absence of endogenous estrogen and increasing concentrations of exogenous E2. T47D cells were plated in 12 well plated at a density of 80,000 cells/well. Two days later culture media were replaced with phenol red-free RPMI containing 5% FBS or 5% DCC-FBS. After 24 hours of starvation, cells were treated with test compounds at increasing concentrations for 48 hours. Apoptosis was assessed by Caspase-Glo assay kit (Promega). The results were expressed as OD±SEM of 2 wells per treatment. B-C, Gene expression of T47D cells in response to EC312 and EC313 for anti and pro-apoptotic genes. T47D cells were grown in phenol red-free RPMI medium containing 5% DCC-FBS for 24 hours and then treated with indicated doses of test compounds alone or in combination with E2 (0.1 nM) (*P<0.01 vs control). D, Effect of EC312 and BZA on the expression of ER, Cyclin D1 and phosphorylation of MAPK and AKT. T47D cells grown in 60-mm culture dishes in phenol red-free RPMI medium containing 5% DCC-FBS and treated with E2 (1 nM) alone or in combination with EC312 or BZA (100 nM) for 24 hours before preparation of cell lysate and analysis by western blot and quantification normalized by beta-actin.

EC313 Reduced E2 Induced Uterine Weight Mammary Gland Ductal Branching in Mice

Figure 5A:
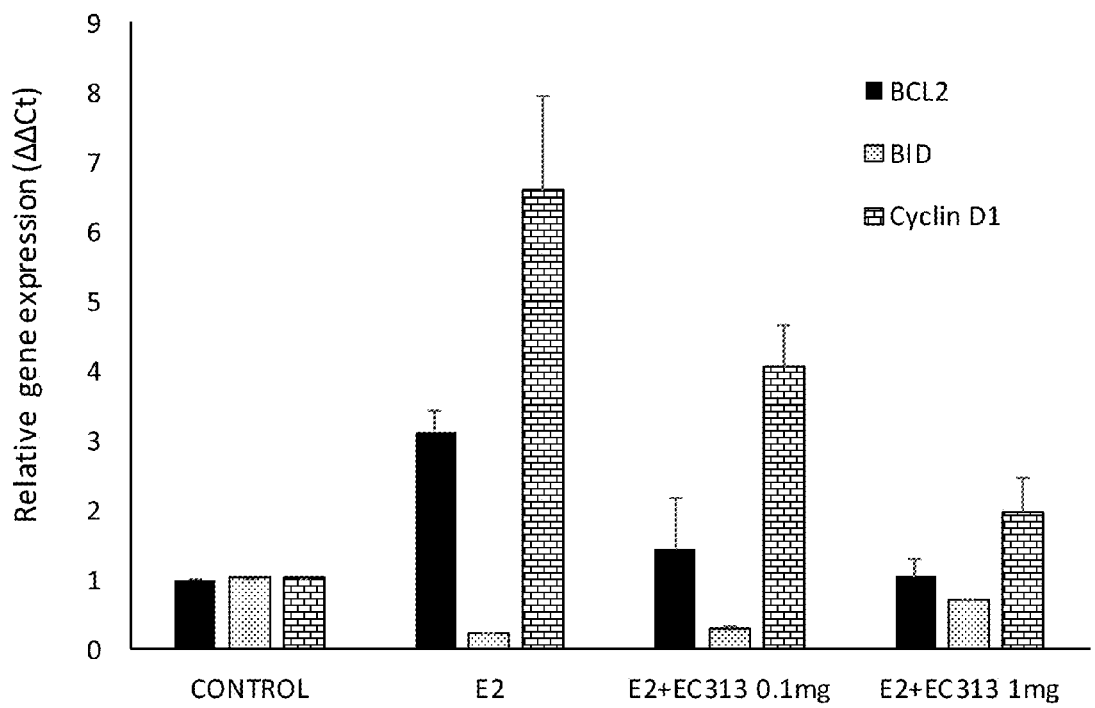
FIGS. 5A-5B depict gene expression in mammary glands of ovariectomized C57BL/6 mice treated with E2, EC313 0.1 and 1.0 mg/kg.
Figure 5B:
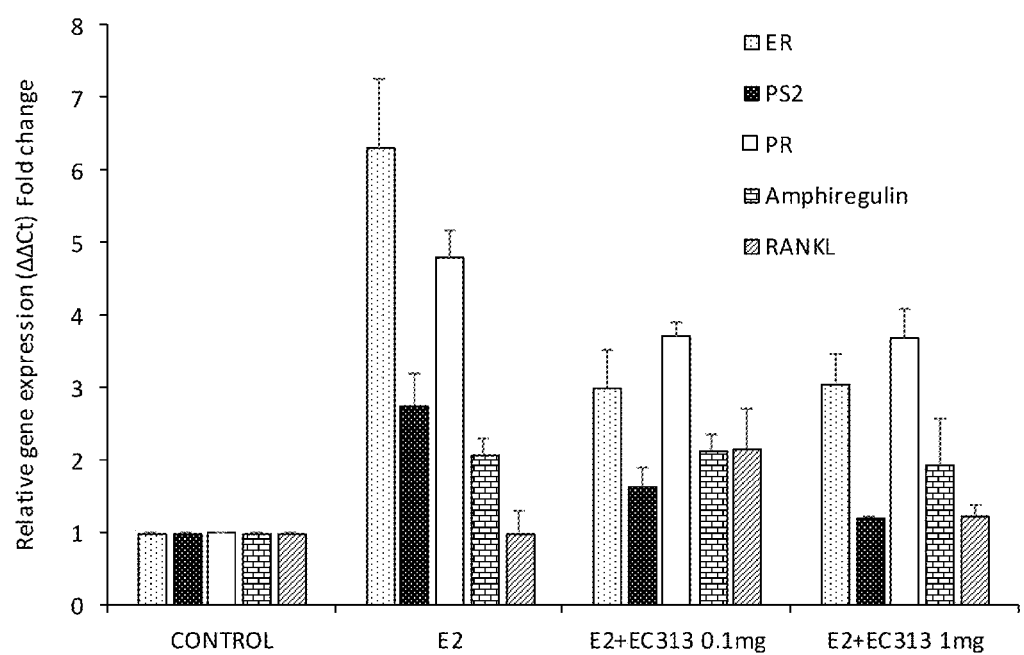

In order to determine the in vivo estrogenic action of EC313 in uterine weight and benign breast development, we have used standard uterine weight bioassay and mammary gland whole mount analysis in ovariectomized mice. E2 stimulated uterine weight was reduced by two fold when combined with EC313 0.1 mg/kg and three fold with 1.0 mg/kg dose of EC313 (FIG. 4 B). Five different measurements were obtained from each whole-mount image. Ductal length (millimeters) was measured by drawing and measuring a straight line caliper from the most distal point of the ductal network to the nipple and end buds were identified as large bulbous profiles located at the termini of ducts. EC313 dose dependently reduced the ductal branching and terminal end buds in whole mount analysis (FIG. 4 A, C, D). The reduced estrogenic effect by the treatment of EC313 was further confirmed by the gene expression studies. The mechanism of EC13 induced apoptosis was confirmed as inhibition of proliferation marker-cyclin D1, anti-apoptotic genes such as BCL2 and pro-apoptotic gene, BID as seen before in in vitro T47D cell model (FIG. 5A). The E2 regulated genes such as cyclin D1 and PS2 were upregulated in the mammary glands of E2 treated animals, whereas those were downregulated with EC313 treatment combined with E2. Since our compounds is an SPRM, the classical PR regulated genes such as amphiregulin (AREG) and RANKL were upregulated in a moderate fashion with EC313 treatment at lower doses but significantly inhibited at higher dose (FIG. 5B).

Our in vivo study revealed that EC313 blocked the estrogenicity of E2 on uterus and mammary gland proliferation including ductal length, terminal end bud development and induced apoptosis. This results were matched with our previous findings classified EC313 as a mesoprogestin (Nickisch et al, 2013). The context dependent progesterone action might help to explain the observed effects of EC313 on T47D breast cancer cells and benign mouse mammary glands.

FIG. 4. A,

Whole mounts of mammary glands of overictomized C57BL/6 mice treated with E2, EC313 0.1 and 1.0 mg/kg. Magnification—upper panel—10×, lower panel—20×. B, Uterine weight of mice treated for 4 weeks with E2, EC313

EC-312 and EC313 were active both as a progestin agonist and antagonist, supporting the guinea pig results and proving that EC-312 and EC313 has a significantly different profile than the currently marketed products. This is especially noteworthy in comparison to CDB 2914 that it didn't show any activity at all at a dose of 3 mg/animal/day. It can be therefore assumed that EC-312 exhibits more than tenfold higher progestational activity than CDB 2914 in this model.

TABLE 3

| Code | Ovulation Inhibition | Uterine Weight at max. | ER-/PR balance vagina. dose (10.mg/day s.c.) | Ovary (CL) | Classification |
|---|---|---|---|---|---|
| RU 486 | ≥3.0 mg | (1.26) | ER-dom ≥1.0 mg | deg. & funct. CL | PR-antagonist |
| CDB 4124 | ≤10.0 | 1.41 | ER-domin. | deg. & funct. CL | PR-antagonist |
| CDB2914 | ≥10.0 mg | (1.01) | ER-domin. | degenerated CL | blunted PR-antagonist |
| EC342 | 10.0 mg | 0.86 | PR-domin | degenerated CL | mesoprogestin |
| EC346 | 0.3 mg | 0.8 | PR-domin | degenerated CL | mesoprogestin |
| EC348 | 10.0 mg | 1.01 | PR-domin | degenerated CL | mesoprogestin |
| EC347 | 10.0 mg | 1.01 | PR-domin | degenerated CL | mesoprogestin |
| EC-312 | ≥0.1 mg | 1.03 | PR-domin. ≥0.1 mg | degenerated CL | mesoprogestin |
| EC-313 | ≥0.1 mg | 1.13 | PR-domin. ≥0.1 mg | degenerated CL | mesoprogestin |
| Controls | 10/11 ovulation | 1.05 | metestrus (9/11) estrus (2/11) | fresh CL | n.a. |

Abbreviations:
corpora lutea (CL):
deg. = degenerating
Signs of ER-Dominance: High uterine weight, vaginal epithelium proliferation of basal layers and cornification of upper layers;
Signs of PR-dominance: absence of ER-dominance, mucification of vaginal epithelium 0.1 and 1.0 mg/kg. Data represented are average uterine weight in milligrams±SD (*P<0.001 vs E2-control). C-D, Total duct length and terminal end bud counts in the mammary gland whole mounts after 4 weeks of the treatment with test compounds (*P<0.001 vs E2-control).

FIG. 5. A-B,

Gene expression in mammary glands of ovariectomized C57BL/6 mice treated with E2, EC313 0.1 and 1.0 mg/kg. Columns are average of relative amount (ΔΔCt) of tested mRNA±SD (n=6) (**P<0.01 vs E2-control, *P<0.001 vs E2-control).

McPhail and Anti McPhail Tests in Rabbits.

Figure 6:
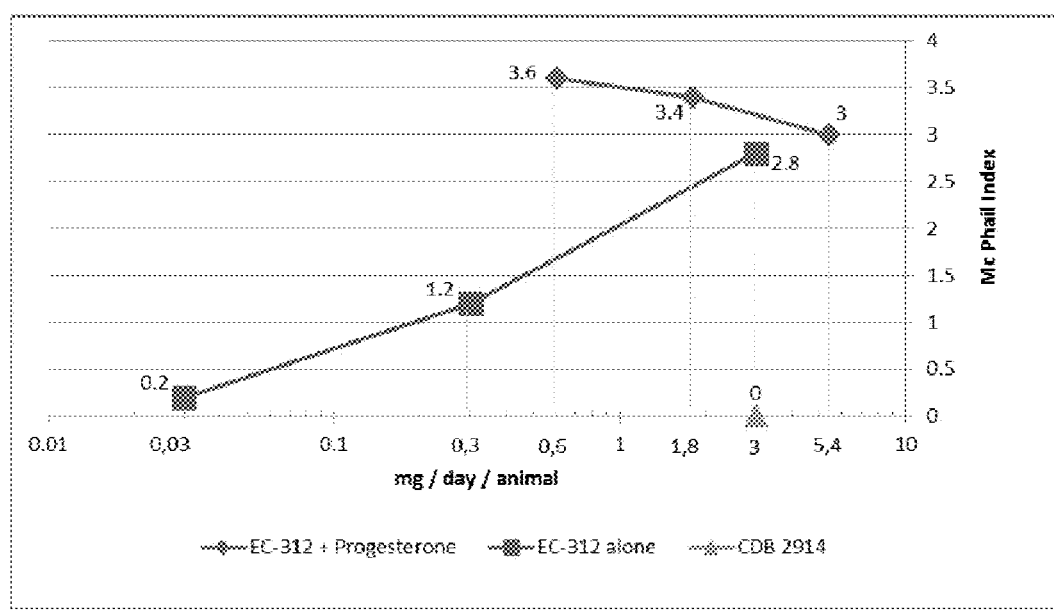
FIG. 6 depicts the results of the McPhail and anti-McPhail tests for EC 312.

The McPhail test in the immature female rabbit is a well-established model to test progestatational and antiprogestational activity [McPhail 1934). Both Ulipristal and CDB 4124 exhibited a higher antiprogestational activity than RU 486 and did not exhibit any progestational activity in the estradiol-primed immature female rabbits. EC-312 and EC313 were also classified as mesoprogestin exhibiting strong agonistic activity in the guinea pig model (Table. 3). The results of the McPhail and anti McPhail test were revealed in FIG. 6 as an example.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A pharmaceutical composition comprising an estrogen and a partial agonistic antiprogestin, wherein the partial agonistic antiprogestin has the formula (I):

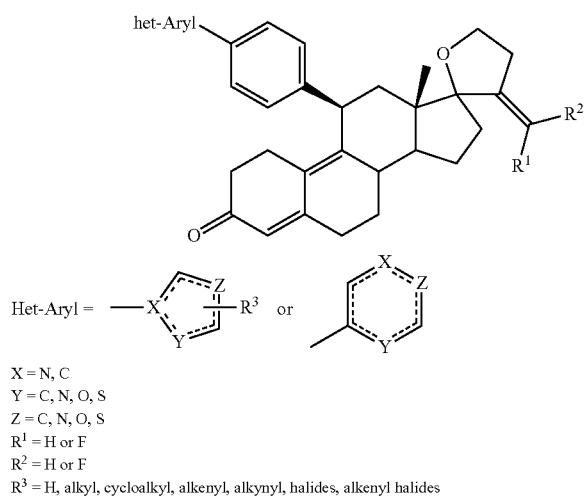

(I)

Het-Aryl = 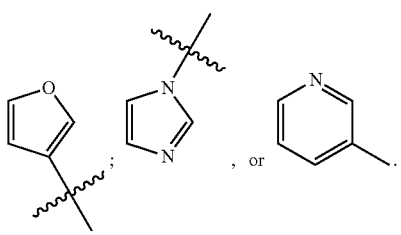

X = N, C
Y = C, N, O, S
Z = C, N, O, S
R$^1$ = H or F
R$^2$ = H or F
R$^3$ = H, alkyl, cycloalkyl, alkenyl, alkynyl, halides, alkenyl halides wherein at least one of X, Y, and Z is not a carbon atom.

2. The pharmaceutical composition of claim 1, wherein the partial agonistic antiprogestin has an EC 50 between 1 nM to 10 nM in a progesterone transactivation assay, carried out on human breast cancer (T47D) cells, for agonistic activity.

3. The pharmaceutical composition of claim 1, wherein the partial agonistic antiprogestin has an EC 50 of between 0.1 nM and 5 nM in a progesterone transactivation assay, carried out on human breast cancer (T47D) cells, for antagonistic activity.

4. The pharmaceutical composition of claim 1, wherein the partial agonistic antiprogestin has an EC 50 between 1 nM to 10 nM in a progesterone transactivation assay, carried out on human breast cancer (T47D) cells, for agonistic activity; and wherein the partial agonistic antiprogestin has an EC 50 of between 0.1 nM and 5 nM in a progesterone transactivation assay, carried out on human breast cancer (T47D) cells, for antagonistic activity.

5. The pharmaceutical composition of claim 1, wherein the partial agonistic antiprogestin shows a ratio of the EC 50 values between agonistic and antagonistic activity in a progesterone transactivation assay, carried out on human breast cancer (T47D) cells, of between 1:0.5 to 1:10.

6. The pharmaceutical composition of claim 1, wherein the partial agonistic antiprogestin is classified as a pure mesoprogestin in the Guinea pig model.

7. The pharmaceutical composition of claim 1, wherein the partial agonistic antiprogestin shows a McPhail index of >2 at doses >1 mg/day.

8. The pharmaceutical composition of claim 1, wherein the estrogen component is selected from the group consisting of: estradiol, estriol, estetrol, and ester derivatives of these compounds.

9. The pharmaceutical composition of claim 1, wherein the partial agonistic antiprogestin has the formula (I), in which:

Het-Aryl is:

10. The pharmaceutical composition of claim 1, wherein the partial agonistic antiprogestin has the formula (I), in which:

Het-Aryl is:

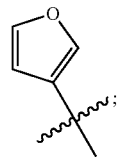 [SMILES: *c1ccoc1]

R$^1$ is F; and R$^2$ is F.

11. The pharmaceutical composition of claim 1, wherein the partial agonistic antiprogestin has the formula (I), in which:

Het-Aryl is:

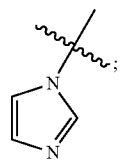 [SMILES: *n1ccnc1]

R$^1$ is F; and R$^2$ is F.

12. The pharmaceutical composition of claim 1, wherein the partial agonistic antiprogestin has the formula (I), in which:

Het-Aryl is:

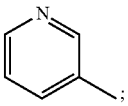

R$^1$ is F; R$^2$ is F.

13. The pharmaceutical composition of claim 1, wherein the partial agonistic antiprogestin is EC 312, EC 313, EC 317; EC 336, or mixtures thereof

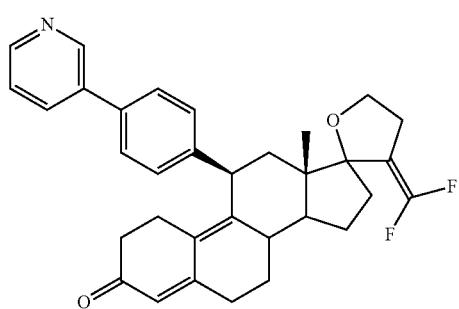
EC-312
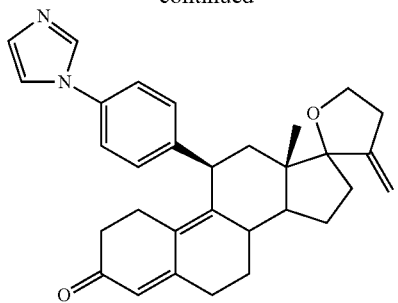
EC-336
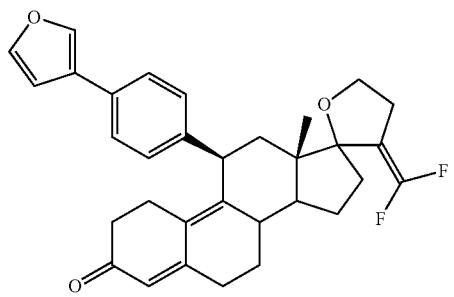
EC-313
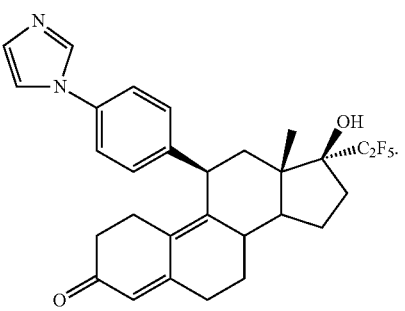
EC-317
\* \* \* \* \*